(12) United States Patent
Hasebe et al.

(10) Patent No.: US 6,706,666 B2
(45) Date of Patent: *Mar. 16, 2004

(54) ENHANCER COMPOSITION FOR AGRICULTURAL CHEMICALS AND AGRICULTURAL CHEMICAL COMPOSITION

(75) Inventors: Keiko Hasebe, Wakayama (JP); Tadayuki Suzuki, Wakayama (JP); Yuichi Hioki, Wakayama (JP)

(73) Assignee: Kao Corporation, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/053,084

(22) Filed: Apr. 1, 1998

(65) Prior Publication Data

US 2001/0029240 A1 Oct. 11, 2001

Related U.S. Application Data

(63) Continuation of application No. 08/507,483, filed as application No. PCT/JP94/02263 on Dec. 27, 1974, now abandoned.

(30) Foreign Application Priority Data

Dec. 28, 1993 (JP) .............................. 5-337502

(51) Int. Cl.$^7$ .................. A01N 57/00; A01N 25/00; A01N 25/02; A01N 25/30; A01N 33/00
(52) U.S. Cl. .................. 504/365; 504/116.1; 504/150; 504/187; 504/188; 504/189; 504/206; 504/358; 504/360; 504/362; 504/363; 504/364; 514/579; 514/613; 514/642; 514/663; 514/772.3; 514/772.6; 514/784; 514/788; 514/836; 514/946; 424/600; 424/DIG. 4
(58) Field of Search .................. 71/DIG. 1; 504/206, 504/358, 362, 363, 364, 365, 116.1, 150, 187.189, 360; 514/784, 579, 613, 642, 663, 772.3, 772.6, 788, 836, 946; 424/600, DIG. 6

(56) References Cited

U.S. PATENT DOCUMENTS

| | | | |
|---|---|---|---|
| 3,998,967 A | 12/1976 | Weil | 514/554 |
| 4,138,483 A | 2/1979 | Gitlitz et al. | 514/186 |
| 4,190,601 A | 2/1980 | Decker et al. | 564/374 |
| 4,888,447 A | 12/1989 | Smith | 564/480 |
| 5,164,179 A | 11/1992 | Hioki et al. | 424/78.08 |
| 5,354,565 A | * 10/1994 | Iwasaki et al. | 424/605 |
| 5,462,912 A | * 10/1995 | Hioki et al. | 504/116 |
| 5,464,806 A | 11/1995 | Kassebaum et al. | 504/206 |
| 5,538,937 A | * 7/1996 | Hasebe et al. | 504/116 |
| 5,563,111 A | * 10/1996 | Hioki et al. | 504/116 |
| 5,622,911 A | * 4/1997 | Hasebe et al. | 504/116 |
| 5,668,085 A | 9/1997 | Forbes et al. | 504/206 |
| 5,728,649 A | * 3/1998 | Hasebe et al. | 504/116 |
| 5,849,663 A | * 12/1998 | Hasebe et al. | 504/116 |
| 5,863,863 A | * 1/1999 | Hasebe et al. | 504/116 |
| 5,863,909 A | * 1/1999 | Kurita et al. | 514/129 |
| 5,948,421 A | * 9/1999 | Okano et al. | 424/405 |
| 6,008,158 A | * 12/1999 | Hasebe et al. | 504/116 |
| 6,030,923 A | * 2/2000 | Okano et al. | 504/116 |
| 6,034,035 A | * 3/2000 | Hasebe et al. | 504/136 |
| 6,093,679 A | * 7/2000 | Azuma et al. | 504/116 |

FOREIGN PATENT DOCUMENTS

| | | |
|---|---|---|
| EP | 0 036106 | 9/1981 |
| EP | 290416 | * 11/1988 |
| EP | 0 274369 | 9/1990 |
| EP | 0 387165 | 9/1990 |
| EP | 04 41764 A | 8/1991 |
| EP | 0 509346 | 10/1992 |
| EP | 0 290416 | 6/1993 |
| EP | 0 597488 | 5/1994 |
| GB | 2 230955 | 11/1990 |
| JP | 55 098105 | 7/1980 |
| JP | 56 135409 | 10/1981 |
| JP | 63 145205 | 6/1988 |
| JP | 2 295907 | 12/1990 |
| JP | 4 502618 | 5/1992 |
| WO | 92/12637 | * 8/1992 |
| WO | WO9 212637 | 8/1992 |

OTHER PUBLICATIONS

Chemical Abstracts 86: 84676, 1977.*
Research Disclosure, vol. 153, pp. 35–36 (Anonymous), Jan. 1977.*

* cited by examiner

Primary Examiner—John Pak
(74) Attorney, Agent, or Firm—Birch, Stewart, Kolasch & Birch, LLP

(57) ABSTRACT

An enhancer composition for agricultural chemicals which can enhance the effectiveness of an agricultural chemical without causing any phytotoxicity to various crops, which comprises at least one nitrogen-containing compound selected from the group consisting of a tertiary amine, a tertiary amine salt and a quaternary ammonium salt and a chelating agent, wherein the content of the chelating agent ranges from 0.01 to 30 mol per mol of the nitrogen-containing compound.

9 Claims, No Drawings

ENHANCER COMPOSITION FOR AGRICULTURAL CHEMICALS AND AGRICULTURAL CHEMICAL COMPOSITION

This application is a continuation of application Ser. No. 08/507,483, filed on Aug. 28, 1995, now abandoned application Ser. No. 08/507,483 is the national phase of PCT International Application No. PCT/JP94/02263 filed on Dec. 27, 1994 under 35 U.S.C. §371. The entire contents of each of the above identified applications are hereby incorporated by reference.

BACKGROUND OF THE INVENTION

1. Field of the Invention

The present invention relates to an enhancer composition for agricultural chemicals, an agricultural chemical composition, a method for enhancing the effectiveness of an agricultural chemical, a use of the above-mentioned enhancer composition for agricultural chemicals for the preparation of an agricultural chemical composition, a use of the above-mentioned enhancer composition for agricultural chemicals for enhancing the effectiveness of an agricultural chemical and an agricultural chemical kit.

2. Description of the Related Art

Agricultural chemicals including insecticides, fungicides (or bactericides), herbicides, miticides (or acaricides) and plant growth regulators have been used in the forms of, for example, emulsions, wettable powders, granules, powders and flowables. In the properties of these agricultural chemical preparations, various attempts have been made to achieve the maximum effectiveness of the agricultural chemicals. However, it has been difficult to enhance the effectiveness of agricultural chemicals through adjustments in formulations. It is further difficult to develop novel agricultural chemicals. Therefore, further enhancement of existing agricultural chemicals would highly contribute to the industry.

As substances capable of enhancing the effectiveness of agricultural chemicals, surfactants comprising various nitrogen-containing compounds such as quaternary ammonium salts, betaines and amine oxides have been known (see European Patent Publication-A No. 274369, published on Jul. 13, 1988). It is known that quaternized or further polyoxyethylenated long-chain amines, among the above-mentioned compounds, are effective for this purpose. However, the enhancement effect of the above described compounds capable of enhancing the effectiveness of agricultural chemicals is not always satisfied.

Since an agricultural chemical is diluted with water prior to use, it contains a chelating agent for trapping metal ions, etc., existing in the water. For example, European Patent Publication-A No. 36106 (published on Sep. 23, 1981) has disclosed a herbicide composition comprising a phosphinothricin derivative, a specific quaternary ammonium salt and a chelating agent. However, particular examples of the quaternary ammonium salts disclosed in this patent include ammonium sulfate, ammonium nitrate, ammonium acetate and the like, and do not include organic quaternary ammonium salts generally used as cationic surfactants. Further, Japanese Patent Publication-A No. 55-98105 (published on Jul. 25, 1980) has disclosed a herbicide composition comprising a bisphosphonic acid herbicide and a chelating agent. However, this patent does not suggest the combination use of an organic quaternary ammonium salt as a cationic surfactant and a chelating agent.

DISCLOSURE OF THE INVENTION

SUMMARY OF THE INVENTION

From a standpoint that the efficacy of an agricultural chemical can be enhanced by using the agricultural chemical together with at least one nitrogen-containing compound selected from the group consisting of a tertiary amine, a tertiary amine salt and a quaternary ammonium salt, the present inventors have conducted extensive studies. As a result, they have found that the efficacies of various agricultural chemicals can be remarkably enhanced by adding a nitrogen-containing compound together with a chelating agent thereto. The present invention has been completed on the basis of this finding.

Thus, the present invention provides an enhancer composition for agricultural chemicals comprising at least one nitrogen-containing compound selected from the group consisting of a tertiary amine, a tertiary amine salt and a quaternary ammonium salt and a chelating agent, wherein the content of the chelating agent ranges from 0.01 to 30 mol per mol of the nitrogen-containing compound. The nitrogen-containing compound is preferably a nitrogen-containing surfactant selected from the group consisting of an organic tertiary amine, an organic tertiary amine salt and an organic quaternary ammonium salt.

Further, the present invention provides an agricultural chemical composition comprising an agricultural chemical, at least one nitrogen-containing compound selected from the group consisting of a tertiary amine, a tertiary amine salt and a quaternary ammonium salt and a chelating agent, wherein the content of the chelating agent ranges from 0.01 to 30 mol per mol of the nitrogen-containing compound and the weight ratio of the total of the nitrogen-containing compound and the chelating agent to the agricultural chemical ranges from 0.05 to 50.

Furthermore, the present invention provides a method for enhancing the effectiveness of an agricultural chemical which comprises applying the above-mentioned enhancer composition for agricultural chemicals with an agricultural chemical to a locus which would be benefit from such treatment, a use of the above-mentioned enhancer composition for agricultural chemicals for the preparation of an agricultural chemical composition, and a use of the above-mentioned enhancer composition for agricultural chemicals for enhancing the effectiveness of an agricultural chemical.

In addition, the present invention provides an agricultural chemical kit which comprises a container containing the above-mentioned enhancer composition for agricultural chemicals and a container containing an agricultural chemical composition, an agricultural chemical kit which comprises a container containing the above-mentioned enhancer composition for agricultural chemicals, a container containing a surfactant other than the above nitrogen-containing compounds and a container containing an agricultural chemical composition, an agricultural chemical kit which comprises a container containing the above-mentioned enhancer composition for agricultural chemicals, a container containing an adjuvant for penetration of agricultural chemicals and a container containing an agricultural chemical composition, and an agricultural chemical kit which comprises a container containing the above-mentioned enhancer composition for agricultural chemicals, a container containing a surfactant other than the above nitrogen-containing compounds, a container containing an adjuvant for penetration of agricultural chemicals and a container containing an agricultural chemical composition.

In this specification, the term "agricultural chemical" means one which is employed as an active or principle ingredient in common agricultural chemical compositions or preparations, and examples thereof include a fungicide (or a bactericide), an insecticide, a miticide (or an acaricide), a herbicide, a plant growth regulator and the like.

Further the scope and the applicability of the present invention will become apparent from the detailed description given hereinafter. However, it should be understood that the detailed description and specific examples which follow, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

[I] Nitrogen-containing compound (A)

Among compounds to be employed as a nitrogen-containing compound in the present invention, examples of the organic tertiary amine include those which will be described below.

(1) Amines represented by the following formula (1):

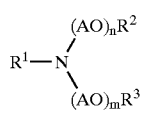
(1)

wherein $R^1$ represents a linear or branched alkyl or alkenyl group having 8 to 22 carbon atoms; each A represents an alkylene group, preferably an alkylene group having 2 to 4 carbon atoms; n and m each represents such a number that the sum of n and m, i.e., the average oxyalkylene number per molecule, is 1 to 40, generally an integer; and $R^2$ and $R^3$ are the same or different from each other and each represents a hydrogen atom or an acyl group (for example, formyl group, acetyl group, propionyl group or benzoyl group).

(2) Amines represented by the following formula (2):

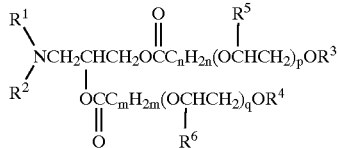
(2)

wherein $R^1$ and $R^2$ are the same or different from each other and each represents an alkyl group having 1 to 4 carbon atoms which may be substituted by a hydroxyl group, preferably an alkyl group having 1 to 4 carbon atoms; $R^3$ and $R^4$ are the same or different from each other and each represents a linear or branched alkyl or alkenyl group having 4 to 36 carbon atoms which may be substituted by a hydroxyl group; each $R^5$ represents a hydrogen atom or a methyl group; each $R^6$ represents a hydrogen atom or a methyl group; m and n are the same or different from each other and each represents a positive number of 1 to 5; and p and q, which generally each represents an average value, are either the same or different from each other and each represents a number of 0 to 30.

(3) Amines represented by the following formula (3):

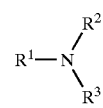
(3)

wherein $R^1$ represents an alkyl group having 1 to 4 carbon atoms which may be substituted by a hydroxyl group; $R^2$ represents a linear or branched alkyl group having 1 to 36 carbon atoms which may be substituted by a hydroxyl group or a linear or branched alkenyl group having 2 to 36 carbon atoms which may be substituted by a hydroxyl group, preferably a linear or branched alkyl or alkenyl group having 5 to 36 carbon atoms which may be substituted by a hydroxyl group, a group represented by the formula: $-C_nH_{2n}-(G^1)-R^4$ (wherein $R^4$ represents a linear or branched alkyl or alkenyl group having 5 to 36 carbon atoms which may be substituted by a hydroxyl group; $G^1$ represents a group represented by the formula: $-OCO-$ or a group represented by the formula: $-NHCO-$; and n represents a positive number of 2 to 6), a group represented by the formula:

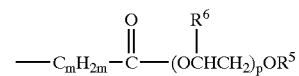

(wherein $R^5$ represents a linear or branched alkyl or alkenyl group having 6 to 36 carbon atoms which may be substituted by a hydroxyl group; each $R^6$ represents a hydrogen atom or a methyl group; m is a positive number of 1 to 5; and p, which generally represents an average value, is a number of 0 to 30) or a group represented by the formula:

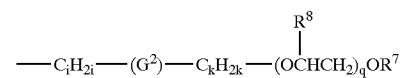

(wherein $R^7$ represents a linear or branched alkyl or alkenyl group having 4 to 36 carbon atoms which may be substituted by a hydroxyl group; each $R^8$ represents a hydrogen atom or a methyl group; $G^2$ represents a group represented by the formula: $-OCO-$ or a group represented by the formula: $-NHCO-$; i represents a positive number of 2 to 6; k represents a positive number of 1 to 5; and q, which generally represents an average value, represents a number of 0 to 30; and $R^3$ represents a group represented by the formula:

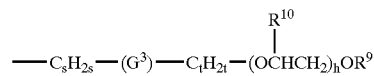

(wherein $R^9$ represents a linear or branched alkyl or alkenyl group having 4 to 36 carbon atoms which may be substituted by a hydroxyl group; each $R^{10}$ represents a hydrogen atom or a methyl group; $G^3$ represents a group represented by the formula: $-OCO-$ or a group represented by the formula: $-NHCO-$; s represents a positive number of 2 to 6; t represents a positive number of 1 to 5; and h, which generally represents an average value, represents a positive number of 0 to 30) or a group represented by the formula:

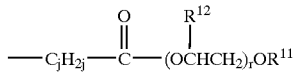

(wherein $R^{11}$ represents a linear or branched alkyl or alkenyl group having 6 to 36 carbon atoms which may be substituted by a hydroxyl group; each $R^{12}$ represents a hydrogen atom or a methyl group; j represents a positive number of 1 to 5; and r, which generally represents an average value, represents a positive number of 0 to 30).

Examples of the tertiary amine salt to be used in the present invention include salts of the above-mentioned organic tertiary amines, for example, inorganic salts thereof such as hydrochlorides, sulfates and nitrates thereof, and organic salts thereof such as carboxylates and sulfonates thereof.

Examples of the quaternary ammonium salt to be used in the present invention include those which will be described below.

(4) Quaternary-ammonium salts represented by the following formula (4):

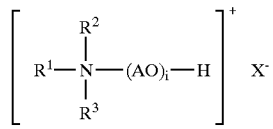

wherein each A represents an alkylene group having 2 or 3 carbon atoms; $R^1$ and $R^2$ are either the same or different from each other and each represents an alkyl group having 1 to 5 carbon atoms; $R^3$ represents an alkyl group having 1 to 5 carbon atoms or a group represented by the formula: $(AO)_j$—H; either i (when $R^3$ is an alkyl group) or the sum of i and j (when $R^3$ is a group represented by the formula: $(AO)_j$—H), which represents the average oxyalkylene number per molecule, is a number of 2 to 20; and $X^-$ is an appropriate counter anion.

As particular examples of the quaternary ammonium salts represented by the above formula (4), those represented by the following formula (4') may be cited:

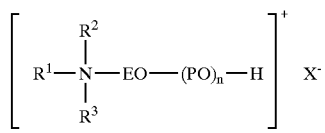

wherein EO represents an oxyethylene group; PO represents an oxypropylene group; $R^1$ and $R^2$ are either the same or different from each other and each represents an alkyl group having 1 to 3 carbon atoms; $R^3$ represents an alkyl group having 1 to 3 carbon atoms or a group represented by the formula: EO—$(PO)_m$—H; either n (when $R^3$ is an alkyl group) or the sum of n and m (when $R^3$ is a group represented by the formula: EO—$(PO)_m$—H), which represents the average oxypropylene number per molecule, is a number of 2 to 20; and $X^-$ is an appropriate counter anion.

(5) Quaternary ammonium salts represented by the following formula (5):

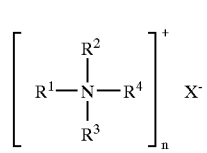

wherein $R^1$, $R^2$, $R^3$ and $R^4$ are either the same or different from one another and each represents a hydrogen atom, an alkyl group having 1 to 4 carbon atoms or a hydroxyethyl group, or two among $R^1$, $R^2$, $R^3$ and $R^4$ form a 3- to 7-membered ring together with the nitrogen atom bonded thereto and —O—, —NH— or —NR— (wherein R represents an alkyl group having 1 to 4 carbon atoms) may substitute for one —$CH_2$— group constituting said 3- to 7-membered ring; $X^-$ represents an anion of inorganic or organic, monobasic or polybasic acid; and n represents 1, 2 or 3 depending on the valence of $X^-$.

(6) Quaternary ammonium salts represented by the following formula (6):

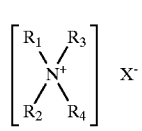

wherein $R_1$ represents a linear or branched alkyl or alkenyl group having 20 to 40 carbon atoms, an alkyl(or alkenyl) arylpolyoxyalkylene, alkyl(or alkenyl)polyoxyethylene or alkyl(or alkenyl)polyoxypropylene group having a linear or branched alkyl or alkenyl group having 20 to 40 carbon atoms, or an acylaminoalkyl or acyloxyalkyl group having a linear or branched acyl group having 20 to 40 carbon atoms; $R_2$ and $R_3$ are either the same or different from each other and each represents a group represented by the formula:

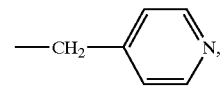

a benzyl group, an alkyl group having 1 to 4 carbon atoms or a hydroxyalkyl group having 2 to 4 carbon atoms; $R_4$ represents an alkyl or alkenyl group having 12 to 30 carbon atoms, an alkylpolyoxyalkylene, alkylarylpolyoxyalkylene, alkylpolyoxyethylene or alkylpolyoxypropylene group having an alkyl group having 12 to 30 carbon atoms, or an acylaminoalkyl or acyloxyalkyl group having an acyl group having 12 to 30 carbon atoms; and $X^-$ represents a counter anion selected from the group consisting of a halide ion, a phosphate group having an alkyl moiety with 1 to 10 carbon atoms, a sulfate group having an alkyl moiety with 1 to 10 carbon atoms and a carboxyl group having an alkyl moiety with 1 to 10 carbon atoms.

(7) Quaternary ammonium salts represented by the following formula (7):

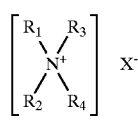

wherein at least one of $R_1$, $R_2$ and $R_3$ is a linear or branched alkyl or alkenyl group having 8 to 30 carbon atoms while the other(s) each represents a methyl group, an ethyl group, a benzyl group, a group represented by the formula:

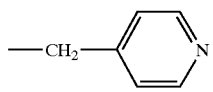

or a group represented by the formula:

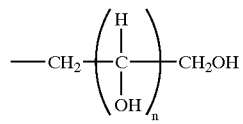

(wherein n is a number of 1 to 5); $R_4$ represents a methyl group or an ethyl group; and $X^-$, which represents a counter ion, is an anionic oligomer or polymer having an average molecular weight of 300 to 20,000 and having an acid type anionic residue, for example, a naphthalene sulfonic acid/formaldehyde condensate.

(8) Quaternary ammonium salts represented by the following formula (8):

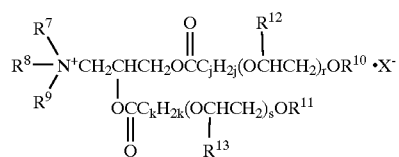

wherein $R^7$ and $R^8$ are either the same or different from each other and each represents an alkyl group having 1 to 4 carbon atoms; $R^9$ represents a hydrogen atom, a benzyl group or an alkyl group having 1 to 4 carbon atoms, preferably an alkyl group having 1 to 4 carbon atoms; $R^{10}$ and $R^{11}$ are either the same or different from each other and each represents a linear or branched alkyl or alkenyl group having 4 to 36 carbon atoms which may be substituted by a hydroxyl group; each $R^{12}$ represents a hydrogen atom or a methyl group; each $R^{13}$ represents a hydrogen atom or a methyl group; j and k are either the same or different from each other and each represents a positive number of 1 to 5; r and s, which generally each represents an average value, are either the same or different from each other and each represents a number of 0 to 30; and $X^-$ is a counter ion.

(9) Quaternary ammonium salts represented by the following formula (9):

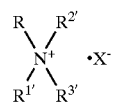

wherein R represents a hydrogen atom, a benzyl group or an alkyl group having 1 to 4 carbon atoms which may be substituted by a hydroxyl group, preferably a hydrogen atom or an alkyl group having 1 to 4 carbon atoms which may be substituted by a hydroxyl group; $R^{1'}$ represents an alkyl group having 1 to 4 carbon atoms which may be substituted by a hydroxyl group; $R^{2'}$ represents a linear or branched alkyl group having 1 to 36 carbon atoms which may be substituted by a hydroxyl group or a linear or branched alkenyl group having 2 to 36 carbon atoms which may be substituted by a hydroxyl group, preferably a linear or branched alkyl or alkenyl group having 5 to 36 carbon atoms which may be substituted by a hydroxyl group, a group represented by the formula: $-C_{n'}-H_{2n'}-(G^{1'})-R^{4'}$ (wherein $R^{4'}$ represents a linear or branched alkyl or alkenyl group having 5 to 36 carbon atoms which may be substituted by a hydroxyl group; $G^{1'}$ represents a group represented by the formula: $-OCO-$ or a group represented by the formula: $-NHCO-$; and n' is a positive number of 2 to 6), a group represented by the formula:

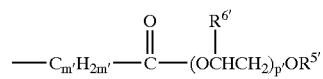

(wherein $R^{5'}$ represents a linear or branched alkyl or alkenyl group having 6 to 36 carbon atoms which may be substituted by a hydroxyl group; each $R^{6'}$ represents a hydrogen atom or a methyl group; m' is a positive number of 1 to 5; and p', which generally represents an average value, is a number of 0 to 30) or a group represented by the formula:

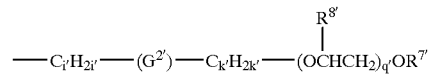

(wherein $R^{7'}$ represents a linear or branched alkyl or alkenyl group having 4 to 36 carbon atoms which may be substituted by a hydroxyl group; each $R^{8'}$ represents a hydrogen atom or a methyl group; $G^{2'}$ represents a group represented by the formula: $-OCO-$ or a group represented by the formula $-NHCO-$; i' is a positive number of 2 to 6; k' is a positive number of 1 to 5; and q', which generally represents an average value, is a number of 0 to 30); $R^{3'}$ represents a group represented by the formula:

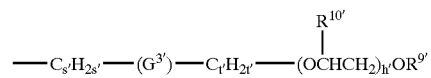

(wherein $R^{9'}$ represents a linear or branched alkyl or alkenyl group having 4 to 36 carbon atoms which may be substituted by a hydroxyl group; each $R^{10'}$ represents a hydrogen atom or a methyl group; $G^{3'}$ represents a group represented by the formula: $-OCO-$ or a group represented by the formula: $-NHCO-$; s' is a positive number of 2 to 6; t' is a positive number of 1 to 5; and h', which generally represents an average value, is a number of 0 to 30), or a group represented by the formula:

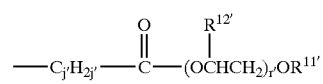

(wherein $R^{11'}$ represents a linear or branched alkyl or alkenyl group having 6 to 36 carbon atoms which may be substituted by a hydroxyl group; each $R^{12'}$ represents a hydrogen atom or a methyl group; j' is a positive number of 1 to 5; and r', which generally represents an average value, is a number of 0 to 30); and $X^-$ is a counter ion.

(10) Quaternary ammonium salts represented by the following formula (10):

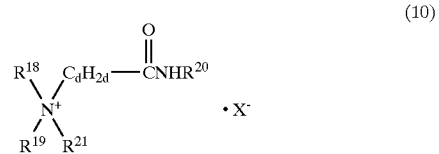

(10)

wherein $R^{18}$ represents a hydrogen atom, a benzyl group or an alkyl group having 1 to 4 carbon atoms which may be substituted by a hydroxyl group, preferably a hydrogen atom or an alkyl group having 1 to 4 carbon atoms which may be substituted by a hydroxyl group; $R^{19}$ represents an alkyl group having 1 to 4 carbon atoms which may be substituted by a hydroxyl group; $R^{20}$ represents a linear or branched alkyl or alkenyl group having 6 to 36 carbon atoms which may be substituted by a hydroxyl group; $R^{21}$ represents a linear or branched alkyl or alkenyl group having 5 to 36 carbon atoms which may be substituted by a hydroxyl group; d is a positive number of 1 to 5; and $X^-$ is a counter ion.

(11) Quaternary ammonium salt represented by the following formula (11):

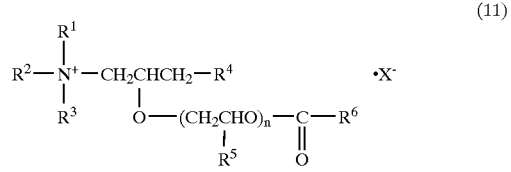

(11)

wherein $R^1$ and $R^2$ are either the same or different from each other and each represents an alkyl group having 1 to 4 carbon atoms, a group represented by the formula:

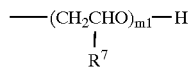

(wherein each $R^7$ represents a hydrogen atom or a methyl group; and m1, which generally represents an average value, is a number of 1 to 30) or a group represented by the formula:

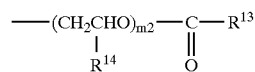

(wherein $R^{13}$ represents a linear or branched alkyl or alkenyl group having 5 to 36 carbon atoms which may be substituted by a hydroxyl group; each $R^{14}$ represents a hydrogen atom or a methyl group; and m2; which generally represents an average value, is a number of 1 to 30); $R^3$ represents a hydrogen atom, a benzyl group or an alkyl group having 1 to 4 carbon atoms, preferably a hydrogen atom or an alkyl group having 1 to 4 carbon atoms; $R^4$ represents a group represented by the formula:

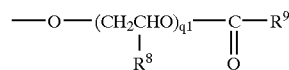

(wherein each $R^8$ represents a hydrogen atom or a methyl group; $R^9$ represents a linear or branched alkyl or alkenyl group having 5 to 36 carbon atoms which may be substituted by a hydroxyl group; and q1, which generally represents an average value, is a number of 0 to 30), a group represented by the formula: —$NHCOR^{10}$ (wherein $R^{10}$ represents a linear or branched alkyl or alkenyl group having 5 to 36 carbon atoms which may be substituted by a hydroxyl group) or a group represented by the formula:

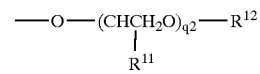

(wherein each $R^{11}$ represents a hydrogen atom or a methyl group; $R^{12}$ represents a linear or branched alkyl or alkenyl group having 5 to 36 carbon atoms which may be substituted by a hydroxyl group; and q2, which generally represents an average value, is a number of 0 to 30); each $R^5$ represents a hydrogen atom or a methyl group; $R^6$ represents a linear or branched alkyl or alkenyl group having 5 to 35 carbon atoms which may be substituted by a hydroxyl group; n, which generally represents an average value, is a number of 0 to 30; and $X^-$ is a counter ion.

Quaternary ammonium salts represented by the above formula (11) includes, for example, those having an oxyalkylene group(s) and those represented by the following formula (11'):

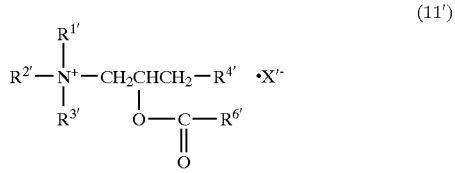

(11')

wherein $R^{1'}$ to $R^{3'}$ are either the same or different from one another and each represents an alkyl or hydroxyalkyl group having 1 to 4 carbon atoms; $R^{4'}$ represents a group represented by the formula: —OCOR (wherein R represents an alkyl or alkenyl group having 14 to 22 carbon atoms); $R^{6'}$ represents an alkyl or alkenyl group having 14 to 22 carbon atoms; and $X^{'-}$ is a counter anion derived from a strong acid.

(12) Quaternary ammonium salts represented by the following formula (12):

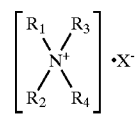

(12)

wherein $R_1$ and $R_2$ are either the same or different from each other and each represents an alkyl group having 1 to 4 carbon atoms or a group represented by the formula:

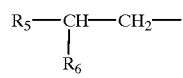

(wherein $R_5$ represents an alkyl or alkenyl group having 4 to 22 carbon atoms; and $R_6$ represents an alkyl or alkenyl group having 2 to 20 carbon atoms), provided that at least one of $R_1$ and $R_2$ represents a group represented by the formula:

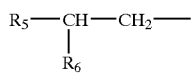

(wherein $R_5$ and $R_6$ each has the same meaning as the one defined above); $R_3$ and $R_4$ are either the same or different from each other and each represents an alkyl group having 1 to 4 carbon atoms; and $X^-$ is a counter anion.

(13) Quaternary ammonium salts represented by the following formula (13):

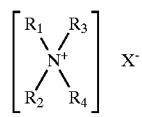

(13)

wherein at least one of $R_1$, $R_2$, and $R_3$ represents an alkyl or alkenyl group having 8 to 30 carbon atoms while the other(s) each represents a methyl group, an ethyl group, a benzyl group, a group represented by the formula:

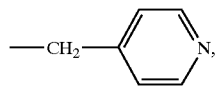

a group represented by the formula: $-(CH_2CH_2O)_n-H$ (wherein n, which generally represents an average value, is a number of 1 to 15, preferably an integer of 1 to 15) or a group represented by the formula:

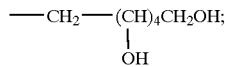

$R_4$ represents a methyl group, an ethyl group or a group represented by the formula: $-CH_2CH_2OH$; and $X^-$, which represents a counter anion, represents a phosphate group, a phosphonate group, a sulfonate group having a hydrocarbon moiety with at least 7 carbon atoms, a sulfate group having a hydrocarbon moiety with at least 7 carbon atoms or an anionic oligomer or copolymer having a degree of polymerization of at least 3 and having an anionic residue.

(14) Quaternary ammonium salts represented by the formula (14):

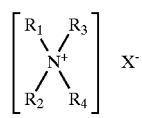

(14)

wherein at least one of $R_1$, $R_2$ and $R_3$ represents a linear or branched alkyl or alkenyl group having 8 to 30 carbon atoms while the other(s) each represents a methyl group, an ethyl group, a benzyl group, a group represented by the formula:

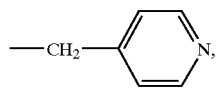

a group represented by the formula: $-(AO)_x-H$ (wherein each A represents an alkylene group, preferably an alkylene group having 2 to 4 carbon atoms; and x, which generally represents an average value, represents a number of 1 to 60, preferably an integer of 1 to 60) or a group represented by the formula:

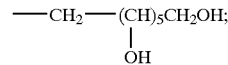

$R_4$ represents a methyl group, an ethyl group or a group represented by the formula: $-CH_2CH_2OH$; and $X^-$, which represents a counter anion, represents a halide ion, a phosphate group, a phosphonate group, a sulfonate group having a hydrocarbon moiety with at least 7 carbon atoms, a sulfate group having a hydrocarbon moiety with at least 7 carbon atoms or an anionic oligomer or copolymer having a degree of polymerization of at least 3 and having an anionic residue.

(15) Quaternary ammonium salts represented by the following formula (15):

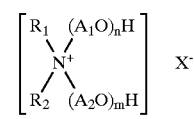

(15)

wherein $R_1$ and $R_2$ are either the same or different from each other and each represents a linear or branched alkyl or hydroxyalkyl group having 1 to 30 carbon atoms or a linear or branched alkenyl group having 2 to 30 carbon atoms; $A_1O$ and $A_2O$ each represents an oxyalkylene group having 2 to 4 carbon atoms; n and m each represents 0 or a positive number, preferably 0 or a positive integer, provided that the sum of n and m, which generally represents an average value, is a number of 1 to 100; and $X^-$ represents a counter ion.

(16) Quaternary ammonium salts represented by the following formula (16):

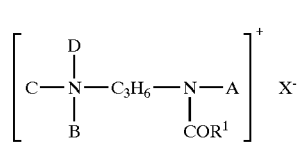

(16)

wherein A represents a hydrogen atom, a group represented by the formula: $-CH_2CH_2-CN$, a group represented by the formula: $-CH_2CH_2COOH$, a group represented by the formula:

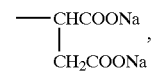

a group represented by the formula:

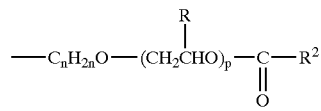

(wherein n is a number of 2 to 9; p, which generally represents an average value, is a number of 0 to 30; each R represents a hydrogen atom or a methyl group; and $R^2$ represents an alkyl or alkenyl group having 4 to 30 carbon atoms), a group represented by the formula:

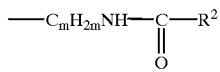

(wherein m is a number of 2 to 9; and $R^2$ has the same meaning as the one defined above) or a group represented by the formula:

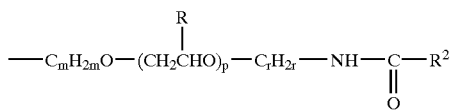

(wherein r is a number of 2 to 6; and m, p, R and $R^2$ each has the same meaning as the one defined above); B, C and D are either the same or different from one another and each represents a hydrogen atom, a methyl group, an ethyl group, a group represented by the formula:

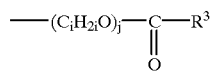

(wherein $R^3$ represents an alkyl or alkenyl group having 4 to 30 carbon atoms; i is a number of 2 to 6; and j, which generally represents an average value, is a number of 1 to 10), a group represented by the formula: —$CH_2COOH$, a group represented by the formula: —$(C_iH_{2i}O)_j$—H (wherein i and j each has the same meaning as the one defined above), a group represented by the formula: —$CH_2COO^-$, a group represented by the formula: —$CH_2CH(OH)CH_2SO_3^-$ or a benzyl group, provided that when one of B, C and D is a group represented by the formula: —$CH_2COO^-$ or a group represented by the formula: —$CH_2CH(OH)CH_2SO_3^-$, then the others are each a groups other than a group represented by the formula: —$CH_2COO^-$ and a group represented by the formula: —$CH_2CH(OH)CH_2SO_3^-$; $R^1$ represents an alkyl or alkenyl group having 4 to 30 carbon atoms; and $X^-$ is a counter ion, provided that when one of B, C and D is a group represented by the formula: —$CH_2COO^-$ or a group represented by the formula: —$CH_2CH(OH)CH_2SO_3^-$, then $X^-$ is absent therefrom.

(17) Quaternary ammonium salts represented by the following formula (17):

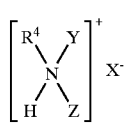

wherein Y and Z are either the same or different from each other and each represents an alkyl or alkenyl group having 6 to 30 carbon atoms, a group represented by the formula:

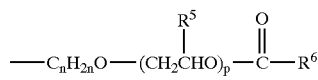

(wherein each $R^5$ represents a hydrogen atom or a methyl group; $R^6$ represents an alkyl or alkenyl group having 5 to 29 carbon atoms; n is a number of 2 to 9; and p, which generally represents an average value, is a number of 0 to 30), a group represented by the formula —$C_3H_6NHCOR^6$ (wherein $R^6$ has the same meaning as the one defined above), a group represented by the formula:

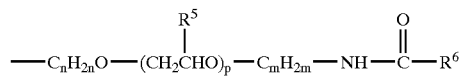

(wherein m is a number of 2 to 9; and n, p, $R^5$ and $R^6$ each has the same meaning as the one defined above), a group represented by the formula: —$C_3H_6OR^6$ (wherein $R^6$ has the same meaning as the one defined above) or a group represented by the formula: —$CH_2CH(OH)CH_2OR^6$ (wherein $R^6$ has the same meaning as the one defined above), provided that Y and Z do not represent alkyl or alkenyl groups having 1 to 4 carbon atoms at the same time; $R^4$ represents an alkyl group having 1 to 4 carbon atoms or a group represented by the formula:

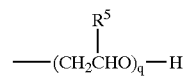

(wherein q, which generally represents an average value, is a number of 1 to 30; and $R^5$ has the same meaning as the one defined above); and $X^-$ is a counter ion.

(18) Quaternary ammonium salts represented by the following formula (18):

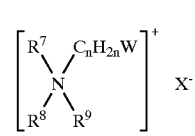

(18)

wherein $R^7$ and $R^8$ are either the same or different from each other and each represents an alkyl group having 1 to 4 carbon atoms, an alkenyl group having 2 to 4 carbon atoms or a group represented by the formula:

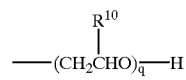

(wherein each $R^{10}$ represents a hydrogen atom or a methyl group; and q, which generally represents an average value, is a number of 1 to 30); $R^9$ represents an alkyl group having 6 to 36 carbon atoms, a group represented by the formula:

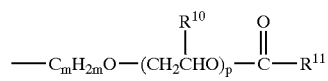

(wherein $R^{11}$ represents an alkyl group having 5 to 35 carbon atoms; m is a number of 2 to 9; p, which generally represents an average value, is a number of 0 to 30; and $R^{10}$ has the same meaning as the one defined above), a group represented by the formula: —$C_mH_{2m}NHCOR^{11}$ (wherein m and $R^{11}$ each has the same meaning as the one defined above) or a group represented by the formula:

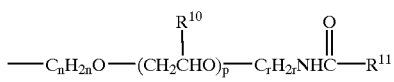

(wherein r is a number of 2 to 6; and m, p, $R^{10}$ and $R^{11}$ each has the same meaning as the one defined above); W represents a group represented by the formula:

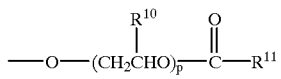

(wherein p, $R^{10}$ and $R^{11}$ each has the same meaning as the one defined above), a group represented by the formula: —NHCOR$^{11}$ (wherein $R^{11}$ has the same meaning as the one defined above) or a group represented by the formula:

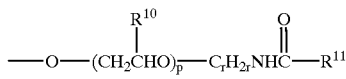

(wherein p, r, $R^{10}$ and $R^{11}$ each has the same meaning as the one defined above); n is a number of 2 to 9; and X$^-$ is a counter ion.

Unless otherwise noted with respect to the counter ions (such as X$^-$) in the above quaternary ammonium salts, they are not particularly restricted. Examples thereof include halide ions such as Cl$^-$, Br$^-$ and I$^-$, alkyl sulfate (RSO$_4^-$) groups, alkylbenzenesulfonate (R-benzene-SO$_3^-$) groups, alkylnaphthalenesulfonate (R-naphthalene-SO$_3^-$) groups, fatty acid residues (RCOO$^-$), alkyl phosphate (ROPO$_3$H$^-$, wherein R represents an alkyl group) groups, anionic oligomers and anionic polymers.

The above compounds can be also classified in the following manner:

(I) compounds represented by the formulae (1), (4), (5), (6), (7), (12), (13), (14) and (15);

(II) compounds represented by the formulae (2), (3), (8), (9) and (10), and compounds represented by the formula (11) excepting those represented by the formula (11');

(III) compounds represented by the formula (11') and (IV) compounds represented by the formulae (16), (17) and (18).

In the present invention, compounds represented by the formulae (6), (7), (12), (13), (14) and (15) are preferably used, compounds represented by the formulae (16), (17) and (18) are still more preferably used, and compounds represented by the formulae (2), (3), (8), (9), (10) and (11) are most preferably used.

It is needless to say that any desired tertiary amines, tertiary amine salts and quaternary ammonium salts other than those cited above can be used in the present invention.

[II] Chelating Agent (B)

The chelating agent to be used in the present invention is not particularly restricted, so long as it is capable of chelating a metal ion. Examples of the chelating agent usable in the present invention include amino polycarboxylic acid chelating agents, aromatic or aliphatic carboxylic acid chelating agents, amino acid chelating agents, ether polycarboxylic acid chelating agents, phosphonic acid chelating agents such as iminodimethylphosphonic acid (IDP) and alkyldiphosphonic acid (ADPA), hydroxy carboxylic acid chelating agents, electrolyte chelating agents of polymer (including oligomer) type, and dimethylglyoxime (DG). These chelating agents may be in the form of either an acid or a salt such as sodium salt, potassium salt and ammonium salt. Alternatively, these chelating agents may be in the form of an ester derivative thereof which can be hydrolyzed.

Examples of the aminopolycarboxylic acid chelating agents include a) compounds represented by the chemical formula of RNX$_2$, b) compounds represented by the chemical formula of NX$_3$, c) compounds represented by the chemical formula of R—NX—CH$_2$CH$_2$—NX—R, d) compounds represented by the chemical formula of R—NX—CH$_2$CH$_2$—NX$_2$, e) compounds represented by the chemical formula of X$_2$N—R'—NX$_2$ and f) compounds similar to compounds of e) and containing four or more Xs, for example, a compound represented by the formula:

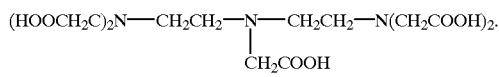

In the above formulae, X represents a group represented by the formula: —CH$_2$COOH or a group represented by the formula: —CH$_2$CH$_2$COOH, R represents a group to be contained in these type, known chelating agents such as a hydrogen atom, an alkyl group, a hydroxyl group and a hydroxyalkyl group, and R' represents a group to be contained in these type, known chelating agents such as an alkylene group and a cycloalkylene group.

Representative examples of the aminopolycarboxylic acid chelating agents include ethylenediaminetetraacetic acid (EDTA), cyclohexanediaminetetraacetic acid (CDTA), nitrilotriacetic acid (NTA), iminodiacetic acid (IDA), N-(2-hydroxyethyl)iminodiacetic acid (HIMDA), diethylenetriaminepentaacetic acid (DTPA), N-(2-hydroxyethyl)ethylenediaminetriacetic acid (EDTA-OH) and glycoletherdiaminetetraacetic acid (GEDTA), and salts thereof.

Examples of the aromatic or aliphatic carboxylic acid chelating agents to be used in the present invention include oxalic acid, succinic acid, pyruvic acid, salicylic acid and anthranilic acid, and salts, methyl esters and ethyl esters thereof. Further, examples of the amino acid chelating agents to be used in the present invention include glycine, serine, alanine, lysine, cystine, cysteine, ethionine, tyrosine and methionine, and salts and derivatives thereof.

Furthermore, examples of the ether polycarboxylic acid chelating agents to be used in the present invention include compounds represented by the following formula, compounds similar to the compounds represented by the following formula and salts (e.g., sodium salt) thereof:

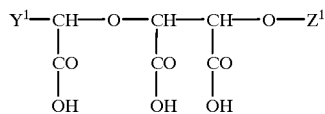

wherein Y$^1$ represents a hydrogen atom, a group represented by the formula: —CH$_2$COOH or a group represented by the formula: —COOH, and Z$^1$ represents a hydrogen atom, a group represented by the formula: —CH$_2$COOH or a group represented by the formula:

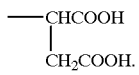

Examples of the hydroxy carboxylic acid chelating agents to be used in the present invention include malic acid, citric acid, glycolic acid, gluconic acid, heptonic acid, tartaric acid, lactic acid and salts thereof.

Examples of the electrolyte chelating agents of polymer (including oligomer) type to be used in the present invention include acrylic acid polymers, maleic anhydride polymers, α-hydroxyacrylic acid polymers, itaconic acid polymers, copolymers comprising at least two of the constituting monomers of these polymers and epoxysuccinic acid polymers.

In addition, chelating agents to be used in the present inveniton further include ascorbic acid and thioglycollic acid, and salts thereof.

Among the above-mentioned chelating agents, preferable ones include aliphatic carboxylic acid chelating agents, aromatic carboxylic acid chelating agents, hydroxy carboxylic acid chelating agents, amino acid chelating agents, ether polycarboxylic acid chelating agents, phosphonic acid chelating agents, electrolyte chelating agents of polymer (including oligomer) type, dimethylglyoxime (DG), ascorbic acid and thioglycollic acid, and salts of ascorbic acid and thioglycollic acid. Among them, aliphatic carboxylic acid chelating agents, aromatic carboxylic acid chelating agents, hydroxy carboxylic acid chelating agents, amino acid chelating agents and ether polycarboxylic acid chelating agents are still more preferable.

In the present invention, such a chelating agent is used in an amount of from 0.01 to 30 mol, preferably from 0.05 to 20 mol and still more preferably from 0.1 to 15 mol, per mol of the above-mentioned nitrogen-containing compound (the total content by mol, when two or more nitrogen-containing compounds are used).

It has been a practice to add a small amount of a chelating agent to a surfactant by which the efficacy of an agricultural chemical can be enhanced [see Japanese Patent Publication-A Nos. 2-295907 (published on Dec. 6, 1990) and 4-502618 (published on May 14, 1992), and European Patent Publication-A No. 36106]. In these cases, however, the addition of the chelating agent aims mainly at trapping substances which are contained in the water for diluting the agricultural chemical and inhibit the activity of the agricultural chemical, namely, trace metal ions (e.g., $Ca^{++}$, $Mg^{++}$) to thereby soften hard water. Therefore, chelating agents are used in the prior art only in a small amount. In contrast, a chelating agent is used in a large amount in the present invention compared with the conventional cases. The present inventors have found for the first time that the efficacy of an agricultural chemical can be remarkably enhanced by using a chelating agent in a larger amount than the conventional dose together with the above-mentioned nitrogen-containing compound.

[III] Enhancer Composition for Agricultural Chemicals

The enhancer composition for agricultural chemicals of the present invention comprises the above-mentioned nitrogen-containing compound (A) and the chelating agent (B). When used in combination with an agricultural chemical, this enhancer composition for agricultural chemicals can enhance the efficacy of the agricultural chemical twice to thrice without causing any phytotoxicity. Namely, the enhancer for agricultural chemicals of the present invention can be safely applied to various crops without causing any phytotoxicity.

Although the mechanism of action of the enhancer composition for agricultural chemicals of the present invention has not been necessarily clarified, it is considered as follows. The nitrogen-containing compounds employed in the present invention are those positively charged in water. Therefore, it specifically adheres to cell membranes of plants, microorganisms and insects, invades the membranes and then abnormally elevates the flowability of the cell membranes, thus causing a disturbance in the membrane functions. As a result, the amount of the agricultural chemical incorporated into the cells is increased and thus the efficacy of the agricultural chemical is enhanced. It is estimated that the chelating agent undergoes some interaction with the nitrogen-containing compound to thereby enhance the efficacy of the agricultural chemical. Accordingly, it seems that the effect of the chelating agent in the present invention essentially differs from the effect, which has hitherto been lectured, of a chelating agent of trapping trace metal ions in water and thus enhancing the efficacy of an agricultural chemical. It has been observed in practice that the effect of a nitrogen-containing compound according to the present invention in enhancing the efficacy of an agricultural chemical is strengthened by adding a chelating agent both in distilled water and in hard water.

In the enhancer composition for agricultural chemicals of the present invention, the dose of the above-mentioned nitrogen-containing compound (A) can be reduced while maintaining the enhancing effect thereof on an agricultural chemical by further using a surfactant (C) other than the nitrogen-containing compounds (A) and/or an adjuvant for penetration of agricultural chemicals (D) therewith.

Examples of the surfactant (C) other than the nitrogen-containing compounds include nonionic surfactants, anionic surfactants and amphoteric surfactants. These surfactants may be used either alone or as a mixture of two or more of them.

Examples of the nonionic surfactants include polyoxyethylene alkyl ethers, polyoxyethylene alkylaryl ethers, polyoxyethylene alkylaryl ether/formaldehyde condensates, polyoxyalkylene aryl ethers, polyoxyalkylene alkyl esters, polyoxyalkylene alkylsorbitol esters, polyoxyalkylene sorbitan esters, polyoxyalkylene alkylglycerol esters, polyoxyalkylene block copolymers, polyoxyalkylene block copolymer/alkylglycerol esters, polyoxyalkylene alkylsulfonamides, polyoxyalkylene rosin esters, polyoxypropylene block copolymers, polyoxyethylene oleyl ethers, polyoxyalkylene alkylphenols, alkylglycosides, alkylpolyglycosides, polyoxyalkylene alkylpolyglycosides, and mixtures comprising two or more of these surfactants.

Among anionic surfactants, typical ones are available in the form of an aqueous solution or a solid. Examples thereof include sodium mono- and dialkylnaphthalenesulfonates, sodium α-olefinsulfonate, sodium alkanesulfonates, alkylsulfosuccinates, alkylsulfates, polyoxyalkylene alkyl ether sulfates, polyoxyalkylene alkyl aryl ether sulfates, polyoxyalkylene styryl phenyl ether sulfates, mono- and dialkylbenzenesulfonates, alkylnaphthalenesulfonates, alkylnaphthalenesulfonate/formaldehyde condensates, alkyl diphenyl ether sulfonates, olefinic sulfonates, mono- and dialkylphosphates, polyoxyalkylene mono- and dialkylphosphates, polyoxyalkylene mono- and diphenyl ether phosphates, polyoxyalkylene mono- and dialkyl phenyl ether phosphates, polycarboxylic acid salts, linear and branched alkyl polyoxyalkylene ether acetic acids and salts thereof, linear and branched alkenyl polyoxyalkylene ether acetic acids and salts thereof, fatty acids and salts thereof, e.g., stearic acid and its salts, oleic acid and its salts, caprylic acid and its salts, capric acid and its salts and lauric acid and its salts, N-methyl fatty acid taurides and mixtures comprising two or more of these surfactants (including sodium, potassium, ammonium and amine salts).

Examples of suitable ampholytic surfactants include lauryldimethylamine oxide, Armox C/12, amine oxides, Monaterics, Miranols, betaines, Lonzaines, other amine oxides and mixtures thereof.

Among these surfactants, nonionic surfactants, anionic surfactants and mixtures of a nonionic surfactant and an anionic surfactants are preferable, and mixtures of a nonionic surfactant and an anionic surfactants are still more preferable. Among these mixtures, those in which the weight ratio of the nonionic surfactant to the anionic surfactant ranges from 1/50 to 50/1 are desired, and those in which the weight ratio ranges from 1/30 to 15/1 are particularly desired.

Among nonionic surfactants, those of the ester type, such as polyoxyalkylene sorbitan esters and polyoxyalkylene alkyl glycerol esters, polyoxyalkylene alkyl ethers and polyoxyalkylene alkylphenyl ethers are preferred, and those of the ester type are particularly preferred from the point of view of environmental conservation, since they are excellent in biodegradability. Among anionic surfactants, polyoxyalkylene alkyl ether sulfates, alkylbenzenesulfonates, and linear and branched alkyl polyoxyalkylene ether acetic acids and salts thereof are preferred and polyoxyalkylene alkyl ether sulfates and linear and branched alkyl polyoxyalkylene ether acetic acids and salts thereof are particularly preferred.

In the enhancer composition for agricultural chemicals comprising a nitrogen-containing compound (A), a chelating agent (B) and a surfactant (C) other than the nitrogen-containing compounds according to the present invention, the weight ratio of the nitrogen-containing compound (A) to the surfactant (C) other than the nitrogen-containing compounds preferably ranges from 1/10 to 50/1, still more preferably from 1/1 to 10/1.

The adjuvant for penetration of agricultural chemicals (D) is used for the efficient penetration of an agricultural chemical into insects, plants, fungi, etc. Examples thereof include those described below.

1) Water including deionized water, aqueous solutions of organic or inorganic acids and aqueous solutions of alkalis.
2) Monohydric alcohols such as methanol, ethanol, n-propanol, isopropanol, n-butanol, isobutanol, isoamyl alcohol, 3-pentanol, n-hexanol, n-heptanol, 2-heptanol, n-octanol, 2-ethylhexanol, n-decanol, undecanol, n-dodecanol, tetradecanol, heptadecanol, cyclohexanol and benzyl alcohol.
3) Polyhydric alcohols and alcohol ethers such as ethylene glycol, ethylene glycol monomethyl ether, ethylene glycol monomethyl acetate, ethylene glycol monoethyl ether, ethylene glycol diethyl ether, ethylene glycol monoethyl ether acetate, ethylene glycol isopropyl ether, ethylene glycol monobutyl ether, ethylene glycol dibutyl ether, ethylene glycol monobutyl ether acetate, ethylene glycol isoamyl ether, ethylene glycol monophenyl ether, ethylene glycol monophenyl ether acetate, ethylene glycol benzyl ether, ethylene glycol monohexyl ether, dimethoxyethanol, ethylene glycol monoacetate, ethylene glycol diacetate, diethylene glycol, 1,3-butylene glycol, diethylene glycol monomethyl ether, diethylene glycol monoethyl ether, diethylene glycol monobutyl ether, diethylene glycol dimethyl ether, diethylene glycol methyl ethyl ether, diethylene glycol diethyl ether, diethylene glycol dibutyl ether, triethylene glycol, triethylene glycol monomethyl ether, propylene glycol, propylene glycol monomethyl ether, propylene glycol monoethyl ether, propylene glycol monobutyl ether, dipropylene glycol monomethyl ether, dipropylene glycol monoethyl ether, butanediol, 2-methyl-2,4-pentanediol, glycerol, glyceryl monoacetate, glyceryl monobutyrate, trimethylolpropane, liquid (at ordinary temperatures) polyethylene glycol, liquid (at ordinary temperatures) polypropylene glycol and polyvinyl alcohol. Among them, preferable ones are polyalkylene glycol monoalkyl ethers and polyalkylene glycol dialkyl ethers, and still more preferable ones are diethylene glycol monoalkyl($C_{1-6}$)ethers, diethylene glycol dialkyl($C_{1-6}$)ethers, triethylene glycol monoalkyl($C_{1-6}$)ethers and triethylene glycol dialkyl($C_{1-6}$)ethers.
4) Halogenated hydrocarbons such as chloroform, carbon tetrachloride, dichloromethane, dichloroethane, trichlorofluoromethane and dichlorodifluoromethane.
5) Ethers such as diethyl ether, diisopropyl ether, dibutyl ether, dihexyl ether, diisoamyl ether, methyl phenyl ether, ethyl phenyl ether, amyl phenyl ether, ethyl benzyl ether, 1,4-dioxane, tetrahydrofuran, tetrahydropyran and polyoxyalkylene phenyl ethers. Among them, preferable ones are polyoxyalkylene phenyl ethers, and still more preferable ones are polyoxyethylene phenyl ethers wherein the number of oxyethylene groups per molecule is from 1 to 10.
6) Ketones such as acetone, methylacetone, methyl ethyl ketone, methyl n-butyl ketone, methyl isobutyl ketone, methyl n-hexyl ketone, diethyl ketone, acetone oil, acetonylacetone, phorone, isophorone, cyclohexanone, methylcyclohexanone and pyrrolidone.
7) Esters such as methyl acetate, ethyl acetate, n-butyl acetate, n-amyl acetate, isoamyl acetate, methylisoamyl acetate, methyl propionate, isoamyl propionate, n-butyl butyrate, butyl stearate, amyl stearate, 2-ethylhexyl oleate, lauryl oleate, oleyl oleate, methyl lactate, ethyl lactate, ethyl benzoate, propyl benzoate, isoamyl benzoate, benzyl abietate, diethyl oxalate, dibutyl oxalate, dimethyl malonate, dimethyl phthalate, diethyl phthalate, dibutyl phthalate, di-2-ethylhexyl phthalate and alkyl trimellitates (e.g., 2-ethylhexyl trimellitate). Among them, preferable ones are alkyl oleates, alkenyl oleates, alkyl phthalates and alkyl trimellitates, and still more preferable ones are alkyl($C_{1-12}$)oleates and alkenyl($C_{2-12}$)oleates.
8) Nitrogen-containing compounds such as formamide, N,N-dimethylformamide, acetonitrile and morpholine.
9) Hydrocarbon compounds such as n-pentane, n-hexane, isohexane, n-heptane, n-octane, n-decane, petroleum ether, petroleum benzine, petroleum fractions (e.g., paraffins, kerosine and gas oil), cyclohexane, toluene, xylene, ethylbenzene, chlorobenzene, cumene, methylnaphthalene and dimethyl sulfoxide.
10) Vegetable oils such as soybean oil and cottonseed oil.

Among these adjuvant for penetrations, polyalkylene glycol monoalkyl ethers and polyalkylene glycol dialkyl ethers are most preferable.

In the enhancer composition for agricultural chemicals comprising a nitrogen-containing compound (A), a chelating agent (B) and an adjuvant for penetration (D) according to the present invention, the weight ratio of the nitrogen-containing compound (A) to the adjuvant, for penetration (D) preferably ranges from 1/5 to 5/1, still more preferably from 1/2 to 2/1. When the ratio exceeds 5/1, the enhancing effect of the adjuvant for penetration (D) is unsatisfactory in contrast, when the ratio is lower than 1/5, the enhancing effect of the adjuvant for penetration (D) is no longer improved and, unfavorably, the combination use of the enhancer composition for agricultural chemicals comprising a nitrogen-containing compound (A), a chelating agent (B) and an adjuvant for penetration (D) according to the present invention with an insecticide or a miticide may cause a serious phytotoxicity to plants.

[IV] Agricultural Chemical Composition

The agricultural chemical composition of the present invention comprises the above-mentioned enhancer composition for agricultural chemicals of the present invention and an agricultural chemical. In this specification, the term "agricultural chemical" means one which is employed as an active or principle ingredient in common agricultural chemical compositions or preparations. The enhancer composition for agricultural chemicals of the present invention, which is employed for preparing the agricultural chemical composition of the present invention, may further comprises a surfactant (C) other than the nitrogen-containing compounds (A) and/or an adjuvant for penetration (D) as described above.

In the agricultural chemical composition of the present invention, the weight ratio of the sum total of the nitrogen-containing compound (A) and the chelating agent (B) to the agricultural chemical(s) is from 0.05 to 50, preferably from 0.05 to 20 and still more preferably from 0.1 to 10. When this ratio is below 0.05, any desired effect of enhancing the effectiveness of the agricultural chemical(s) can not be fully achieved. When this ratio exceeds 50, on the other hand, the enhancing effect is no longer improved.

Next, examples of the agricultural chemicals to be used in the agricultural chemical composition of the present invention will be cited, though the agricultural chemicals to be used in the present invention is not restricted thereto.

In the case of fungicides (or bactericides), included are Zineb [zinc ethylenebis(dithiocarbamate)], Maneb [manganese ethylenebis(dithiocarbamate)], Thiram [bis(dimethylthiocarbamoyl)disulfide], Mancozeb [complex of zinc and manganese ethylenebis(dithiocarbamate)], Polycarbamate [dizinc bis(dimethyldithiocarbamate)ethylenebis(dithiocarbamate)], Propineb [polymeric zinc propylenebis(dithiocarbamate)], benzimidazole fungicides such as Benomyl [methyl 1-(butylcarbamoyl)-2-benzimidazolecarbamate] and Thiophanate-methyl [1,2-bis(3-methoxycarbonyl-2-thioureido)benzene]; Vinclozolin [3-(3,5-dichlorophenyl)-5-methyl-5-vinyl-1,3-oxazolidine-2,4-dione], Iprodione [3-(3,5-dichlorophenyl)-N-isopropyl-2,4-dioxoimidazolidine-1-carboxamide], Procymidone [N-(3,5-dichlorophenyl)-1,2-dimethylcyclopropane-1,2-dicarboximide], Anilazine (Triazine) [2,4-dichloro-6-(2-chloroanilino)-1,3,5-triazine], Triflumizole [(E)-4-chloro-α,α,α-trifluoro-N-(1-imidazol-1-yl-2-propoxyethylidene)toluidine], Metalaxyl [methyl N-(2-methoxyacetyl)-N-(2,6-xylyl)-DL-alaninate], Bitertanol [all-rac-1-(biphenyl-4-yloxy)-3,3-dimethyl-1-(1H-1,2,4-triazol-1-yl)-2-butan-2-ol], Pyrifenox [2',4'-dichloro-2-(3-pyridyl)acetophenone (EZ)-O-methyloxime], Fenarimol [2,4'-dichloro-α-(pyridin-5-yl)benzhydryl alcohol], Triforine [1,4-bis-(2,2,2-trichloro-1-formamidoethyl)piperazine], Iminoctadine acetate [1,1'-iminiodi(octamethylene)diguanidinium triacetate], organocopper compound (Oxine-copper [copper 8-quinolinolate]), antibiotic bactericides (streptomycin type, tetracycline type, polyoxins type, blasticidin S, kasugamycin type, validamycin type), Triadimefon [1-(4-chlorophenoxy)-3,3-dimethyl-1-(1,2,4-triazol-1-yl)-2-butanone], Isoprothiolane [diisopropyl 1,3-dithiolan-2-ylidene-malonate], Chlorothalonil (Daconil) [tetrachloroisophthalonitrile], Etridiazol (Pansoil) [5-ethoxy-3-trichloromethyl-1,2,4-thiadiazole], Fthalide [4,5,6,7-tetrachlorophthalide], Iprobenfos (Kitazin P) [O,O-diisopropyl-S-benzyl thiophosphate], Edifenphos (Hinosan) [O-ethyl S,S-diphenyl dithiophosphate], Probenazole [3-allyloxy-1,2-benzisothiazole-1,1-dioxide], Captan [N-trichloromethylthiotetrahydrophthalimide] and Fosetyl [aluminum tris(ethylphosphonate)].

In the case of insecticides, included are pyrethroid insecticides such as Fenvalerate [α-cyano-3-phenoxybenzyl 2-(4-chlorophenyl)-3-methylbutanoate] and Cyfluthrin (Baythroid) [α-cyano-4-fluoro-3-phenoxyphenylmethyl 3-(2,2-dichloroethenyl)-2,2-dimethylcyclcopropanecarboxylate]; organophosphorus insecticides such as Dichlorvos (DDVP) [dimethyl 2,2-dichlorovinyl phosphate], Fenitrothion (MEP) [O,O-dimethyl-O-(3-methyl-4-nitrophenyl)thiophosphate], Malathion (Malathon) [S-[1,2-bis(ethoxycarbonyl)ethyl] dimethyl phosphorothiol-thionate], Dimethoate [dimethyl S-(N-methylcarbamoylmethyl)dithiophosphate], Phenthoate (Elsan) [S-[α-(ethoxycarbonyl)benzyl]dimethyl phosphorothiol-thionate] and Fenthion (Baycid) [O,O-dimethyl-O-[3-methyl-4-(methylthio)phenyl]thiophosphate]; carbamate insecticides such as Fenobucarb (Bassa) [O-sec-butylphenyl methylcarbamate], Metolcarb (MTMC) [m-tolyl methylcarbamate], Xylylcarb (Meobal) [3,4-dimethylphenyl N-methylcarbamate] and Carbaryl (NAC) [1-naphthyl N-methylcarbamate]; Methomyl [S-methyl N-(methylcarbamoyloxy)thioacetimidate] and Cartap [1,3-bis(carbamoylthio)-2-(N,N-dimethylamino)propane hydrochloride].

Further, in the case of natural insecticides, included are pyrethrin preparations, which originate from *Chrysanthemum cinerariaefolium,* rotenone preparations, which originate from Derris which is a shrub of the pulse family, and nicotine preparations [containing 3-(1-methyl-2-pyrrolidinyl)pyridine sulfate]. In the case of insect growth regulators (IGR), included are diflubenzuron [1-(4-chlorophenyl)-3-(2,6-difluorobenzoyl)urea], teflubenzuron [1-(3,5-dichloro-2,4-difluorophenyl)-3-(2,6-difluorobenzoyl)-urea], chlorofluazuron [1-[3,5-dichloro-4-(3-chloro-5-trifluoromethyl-2-pyridyloxy)phenyl]-3-(2,6-difluorobenzoyl)urea], buprofezin [2-tert-butylimino-3-isopropyl-5-phenyl-3,4,5,6-tetrahydro-2H-1,3,5-thiadiazin-4-one] and fenoxycarb [ethyl 2-(4-phenoxyphenoxy)ethylcarbamate].

In the case of miticides (or acaricides), included are Pyridaben [2-tert-butyl-5-(4-tert-butylbenzylthio)-4-chloropyridazin-3(2H)-one], Acricid [2,4-dinitro-6-sec-butylphenyldimethylacrylate], Chloromite [isopropyl 4,4-dichlorobenzylate], Chlorobenzilate (Akar) [ethyl 4,4'-dichlorobenzilate], Dicofol (Kelthane) [1,1-bis(p-chlorophenyl)-2,2,2-trichloroethanol], Benzoximate (Citrazon) [ethyl-O-benzoyl-3-chloro-2,6-dimethoxybenzohydroximate], Propargite (Omite) [2-(p-tert-butylphenoxy)cyclohexyl 2-propynyl sulfite], Fenbutatin Oxide (Osadan) [hexakis(β,β-dimethylphenylethyl)distannoxane], Hexythiazox [trans-5-(4-chlorophenyl)-N-cyclohexyl-4-methyl-2-oxothiazolidine-3-carboxamide] and Amitraz [3-methyl-1,5-bis(2,4-xylyl)-1,3,5-triazapenta-1,4-diene].

In the case of herbicides, included are acid amide hebicides such as Propanil (DCPA) [3',4'-dichloropropionanilide] and Alachlor [2-chloro-2',6'-diethyl-N-(methoxyethyl)acetanilide]; urea herbicides such as Diuron (DCMU) [3-(3,4-dichlorophenyl)-1,1-dimethylurea] and Linuron [3-(3,4-dichlorophenyl)-1- methoxy-1-methylurea); dipyridyl herbicides such as Paraquat Dichloride (Paraquat)-[1,1'-dimethyl-4,4'-bipyridirium dichloride] and Diquat Dibromide (Diquat) [6,7-dihydrodipyrido[1,2-a:2',1'-c]-pyrazindiium dibromide]; diazine herbicides such as Bromacil [5-bromo-3-sec-butyl-6-methyluracil]; S-triazine herbicides such as Simazine [2-chloro-4,6-bis(ethylamino)-1,3,5-triazine] and Simetryn [2,4-bis(ethylamino)-6-methylthio-1,3,5-triazine]; nitrile herbicides such as Dichlobeni (DBN) [2,6-dichlorobenzonitrile]; dinitroaniline herbicides such as Trifluralin [α,α,α-trifluoro-2,6-dinitro-N,N-dipropyl-p-toluidine]; carbamate herbicides such as Benthiocarb [S-p-chlorobenzyl diethylthiocarbamate] and MCC [methyl 3,4-dichlorocarbanilate]; diphenylether herbicides such as Nitrofen (NIP) [2,4-dichlorophenyl-p-nitrophenylether]; phenol herbicides such as PCP [pentachlorophenol]; benzoic acid herbicides such as Dicamba (MDBA) [3,6-dichloro-2-methoxybenzoic acid dimethylamine salt]; phenoxy herbicides such as 2,4-D [2,4-dichlorophenoxyacetic acid and salts (sodium, amine and ethylether) thereof], and Mapica (MCPCA) [2'-chloro-2-(4-chloro-o-tolyloxy)acetanilide]; organic phosphorus herbicides such as Glyphosate [N-(phosphonomethyl)glycine] and salts thereof, Bialaphos [sodium salt of L-2-amino-4-[(hydroxy)(methyl) phosphinoyl]butyryl-L-alanyl-L-alanine) and Glufosinate [ammonium DL-homoalanin-4-yl (methyl)phosphinate], and aliphatic herbicides such as TCA [trichloroacetic acid and salts thereof].

In the case of plant growth regulators, included are MH (maleic hydrazide), Ethephon [2-chloroethylphosphonic acid], UASTA and Bialaphos.

In the present invention, it is preferable to use a fungicide, an insecticide, a miticide or a plant growth regulator as the agricultural chemical. When a herbicide is used as the agricultural chemical, it is preferable to use one other than organophosphorus herbicides.

The agricultural chemical composition of the present invention may be formulated into any preparation such as liquid preparations, emulsions, wettable powders, granules, powders and flowables without any limitation. Accordingly, the agricultural chemical composition of the present invention may contain other additives which are selected depending on the formulation or preparation, for example, emulsifiers, dispersing agents and carriers.

The agricultural chemical composition according to the present invention may further contain a pH regulator, an inorganic salt or a thickener, if required.

Examples of the pH regulators to be used in the present invention include citric acid, phosphoric acid (e.g., pyrophosphoric acid) and gluconic acid, and salts thereof.

Examples of the inorganic acid salts to be used in the present invention include inorganic mineral salts such as clay, talc, bentonite, zeolite, calcium carbonate, diatomaceous earth and white carbon, and inorganic ammonium salts such as ammonium sulfate, ammonium nitrate, ammonium phosphate, ammonium thiocyanate, ammonium chloride and ammonium sulfamate.

In addition, examples of thickeners to be used in the present invention include natural, semisynthetic and synthetic, water-soluble thickeners. As natural mucilaginous matters, xanthane gum and zanflow, which are derived from microorganism, and pectine, gum arabic and guar gum, which are derived from plant, are cited. As semisynthetic mucilaginous matters, methylated, carboxyalkylated and hydroxyalkylated products of cellulose such as methylcellulose, carboxymethylcellulose and hydroxymethylcellulose, methylated, carboxyalkylated and hydroxyalkylated products of starch derivatives, and sorbitol are cited. Furthermore, polyacrylates, polymaleates, polyvinylpyrrolidone and pentaerythritol/ethyleneoxide adducts are cited as synthetic mucilaginous matters.

The agricultural chemical composition of the present invention may further contain one or more ingredients such as plant growth regulators other than those cited above, fertilizers and preservatives.

The agricultural chemical composition of the present invention is used in order to control fungi (or bacteria), insects, mites (or acarids) and herbs or to regulate the growth of plants.

The agricultural chemical kit according to the present invention comprises a container containing the enhancer composition according to the present invention and another container containing an agricultural chemical composition. In this case, the enhancer composition may comprise at least one nitrogen-containing compound (A) selected from the group consisting of a tertiary amine, a tertiary amine salt and a quaternary ammonium salt and a chelating agent. The enhancer composition may further comprise a surfactant (C) other than the nitrogen-containing compounds (A) and/or an adjuvant for penetration (D). Alternatively, another agricultural chemical kit according to the present invention comprises a container containing at least one nitrogen-containing compound (A) selected from the group consisting of a tertiary amine, a tertiary amine salt and a quaternary ammonium salt and a chelating agent (B), a container containing a surfactant (C) other than the nitrogen-containing compounds (A) and a container containing an agricultural chemical composition. The container containing at least one nitrogen-containing compound (A) and a chelating agent (B) and/or the container containing a surfactant (C) may further contain an adjuvant for penetration (D). Furthermore, an agricultural chemical kit which comprises a container containing at least one nitrogen-containing compound (A) selected from the group consisting of a tertiary amine, a tertiary amine salt and a quaternary ammonium salt and a chelating agent (B), a container containing an adjuvant for penetration (D) and a container containing an agricultural chemical composition, and another agricultural chemical kit which comprises a container containing at least one nitrogen-containing compound (A) selected from the group consisting of a tertiary amine, a tertiary amine salt and a quaternary ammonium salt and a chelating agent (B), a container containing a surfactant (C) other than the nitrogen-containing compounds (A), a container containing an adjuvant for penetration (D) and a container containing an agricultural chemical composition, are included in the scope of the present invention.

The "agricultural chemical composition" which is a constituent of the kit is a composition which comprises an agricultural chemical(s), is free from the nitrogen-containing compound (A) and is in the form of, for example, an emulsion, a liquid or a wettable powder. The agricultural chemical composition may contain a small amount of the chelating agent (B).

In the agricultural chemical kit according to the present invention, a composition comprising an agricultural chemical is separated from the enhancer composition for agricultural chemicals comprising a nitrogen-containing compound (A) and a chelating agent (B) according to the present invention. Namely, the agricultural chemical composition which is a constituent of the kit differs from the agricultural chemical composition of the present invention which comprises the enhancer composition for agricultural chemicals according to the present invention and an agricultural chemical(s) in admixture.

Each of contents in these containers is not restricted in their form but appropriately prepared depending on the use and purpose. The material of the container is not restricted so long as it is not react with or affect the content. Examples of the material include plastics, glass, foil, etc.

The enhancer composition according to the present invention is applied with an agricultural chemical to a locus which would benefit from such treatment, i.e., the application of the enhancer composition and the agricultural chemical. In general, the enhancer composition and the agricultural chemical are used with water or a liquid carrier. As means for applying the enhancer composition for agricultural chemicals according to the present invention, (1) one wherein the agricultural chemical composition of the present invention containing the nitrogen-containing compound (A) and the chelating agent (B) and having a preparation form is used (if necessary, the agricultural chemical composition is diluted with, for example, tap water), (2) another one wherein the enhancer composition of the present invention is added to an agricultural chemical composition, which has been diluted with water, and (3) another one wherein the enhancer composition of the present invention is diluted with water and then an agricultural chemical composition is diluted with the resultant diluted solution of the enhancer composition, are useful. The desired enhancement effect can be achieved by either means.

The agricultural chemical composition of the present invention includes one containing the agricultural chemical in high concentration, the nitrogen-containing compound (A) in high concentration and the chelating agent (B) in high concentration, and another one containing the agricultural chemical in an appropriate concentration for application, the nitrogen-containing compound (A) in an appropriate concentration for application and the chelating agent (B) in an appropriate concentration for application. When the former is used, the agricultural chemical composition is diluted with water, etc., for example, just before applying. On the other hand, the agricultural chemical compositions used in the above cases (2) and (3) include those containing the agricultural chemical in high concentration and being free from the nitrogen-containing compound (A).

The contents of the agricultural chemical, the nitrogen-containing compound (A) and the chelating agent (B) in the diluted solution are not limited. The content of the agricultural chemical in the diluted solution depends on, for example, the kind of the agricultural chemical and its use. While the contents of the nitrogen-containing compound (A) and the chelating agent (B) in the diluted solution depends on, for example, the kind of the agricultural chemical to be mixed.

The diluted liquid comprising an appropriate amount of an agricultural chemical, an appropriate amount of the nitrogen-containing compound (A) and an appropriate amount of the chelating agent (B) is applied to, for example, plants, crops, vegetables, fruits, trees, fruit trees, grasses, weeds or seeds, and, at the same time, to fungi, bacteria, insects, acarids or mites. In other words, the diluted liquid is applied to a farm, a plantation, a fruit garden, an orchard, a flower garden, a lawn, a wood and a forest.

EXAMPLES

The present invention will now be described in more detail with reference to the following Examples which should not be considered to limit the scope of the present invention.

Example 1

Use was made of the organic tertiary amines and salts thereof and the quaternary ammonium salts as specified in Tables 1 and 2, and the chelating agents and surfactants as specified in Tables 3, 4-1 and 4-2 to thereby give various enhancer compositions for agricultural chemicals as listed in Tables 3, 4-1 and 4-2.

TABLE 1

| Compd. no. | Organic tertiary amine or its salt |
| --- | --- |
| 1 | $C_{12}H_{25}-N\begin{pmatrix}(CH_2CH_2O)_nH\\(CH_2CH_2O)_mH\end{pmatrix}$ (n + m = 15) |
| 2 | $C_{12}H_{25}-\underset{O}{\overset{}{C}}-\underset{H}{\overset{}{N}}-(CH_2)_3-\overset{+}{N}\begin{pmatrix}CH_3\\H\;CH_3\end{pmatrix} \cdot Cl^-$ |
| 3 | $\begin{matrix}CH_3\\\overset{+}{N}\\CH_3\;H\end{matrix}-CH_2-\underset{OCO-C_9H_{19}}{\overset{}{CH}}-CH_2-OCO-C_9H_{19} \cdot Cl^-$ |
| 4 | $\begin{matrix}CH_3\\\overset{+}{N}\\H\end{matrix}\begin{matrix}C_2H_4-OCO-C_7H_{15}\\C_3H_6-NHCO-C_7H_{15}\end{matrix} \cdot CH_3COO^-$ |

TABLE 1-continued

| Compd. no. | Organic tertiary amine or its salt |
|---|---|
| 5 | 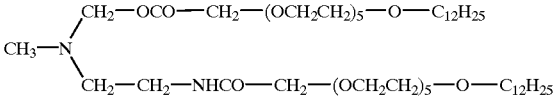 |

TABLE 2

| Compd. no. | Organic quaternary ammonium salt |
|---|---|
| 6 | $C_{12}H_{25}$—$N^+$(CH$_3$)—[(CH$_2$CH$_2$O)$_n$H][(CH$_2$CH$_2$O)$_m$H] · Cl$^-$   (n + m = 15) |
| 7 | (CH$_3$)$_2$N$^+$(C$_{10}$H$_{21}$)$_2$ · [naphthalene with CH$_3$, CH$_2$— and SO$_3^-$ substituents]$_{10}$ |
| 8 | (CH$_3$)$_2$N$^+$[CH$_2$CH$_2$—OCO—CH$_2$—(OCH$_2$CH$_2$)$_5$—O—C$_{12}$H$_{25}$][CH$_2$—CO—(OCH$_2$CH$_2$)$_6$—O—C$_{12}$H$_{25}$] · Cl$^-$ |
| 9 | (CH$_3$)$_2$(C$_2$H$_5$)N$^+$—CH$_2$—CH(OCO—C$_7$H$_{15}$)—CH$_2$—OCO—C$_7$H$_{15}$ · C$_2$H$_5$SO$_4^-$ |
| 10 | (CH$_3$)$_2$N$^+$(CH$_2$—COO—C$_{12}$H$_{25}$)$_2$ · Cl$^-$ |
| 11 | (CH$_3$)(C$_{10}$H$_{21}$)N$^+$(CH$_3$)[CH$_2$—CO—(OCH$_2$CH$_2$)$_8$—O—C$_{12}$H$_{25}$] · Cl$^-$ |
| 12 | (C$_{12}$H$_{25}$)(CH$_2$CH$_2$OH)$_2$N$^+$—CH$_2$—C$_6$H$_5$ · Cl$^-$ |

TABLE 2-continued

| Compd. no. | Organic quaternary ammonium salt |
|---|---|
| 13 | $(CH_3)_3N^+-CH_2-CH(CH_2-OCO-CH_2-O(CH_2CH_2O)_{10}-C_{16}H_{33})-CH_2-OCO-CH_2-O(CH_2CH_2O)_{10}-C_{16}H_{33} \cdot CH_3SO_4^-$ |

TABLE 3

| | Formulation no. | Compd. (A) no. | Chelating agent (B) added | (B)/(A) by mol | Surfactant (C) used | (A)/(B)/(C) by wt. |
|---|---|---|---|---|---|---|
| Invention product | 1 | 1 | EDTA-4Na | 0.50 | — | 80/20/0 |
| | 2 | 1 | EDTA-4Na | 0.38 | POE(10) nonylphenyl ether | 70/10/20 |
| | 3 | 1 | EDTA-4Na | 0.38 | POE(20) sorbitan monooleate | 70/10/20 |
| | 4 | 2 | IDA-2Na | 0.50 | — | 80/20/0 |
| | 5 | 2 | IDA-2Na | 0.45 | POE(9) nonylphenyl ether | 75/15/10 |
| | 6 | 2 | DTPA-5Na | 0.08 | POE(6) lauryl ether | 80/10/10 |
| | 7 | 3 | NTA-3Na | 0.45 | — | 80/20/0 |
| | 8 | 3 | NTA-3Na | 0.26 | POE(6) sorbitan monolaurate | 70/10/20 |
| | 9 | 3 | NTA-3Na | 0.26 | POE(25) hardened castor oil | 70/10/20 |
| | 10 | 4 | EGTA-4Na | 0.25 | — | 80/20/0 |
| | 11 | 4 | EGTA-4Na | 0.21 | POE(10) nonylphenyl ether | 70/15/15 |
| | 12 | 4 | EGTA-4Na | 0.21 | POE(10) octylphenyl ether | 70/15/15 |
| | 13 | 5 | DTPA-5Na | 0.44 | — | 80/20/0 |
| | 14 | 5 | DTPA-5Na | 0.35 | POE(9) nonylphenyl ether | 75/15/10 |
| | 15 | 5 | DTPA-5Na | 0.35 | POE(6) sorbitan monooleate | 75/15/10 |
| | 16 | 6 | CDTA-4Na | 0.56 | — | 80/20/0 |
| | 17 | 6 | CDTA-4Na | 0.25 | POE(10) oleate | 70/10/20 |
| | 18 | 6 | CDTA-4Na | 0.25 | POE(10) nonylphenyl ether | 70/10/20 |

TABLE 4

| | Formulation no. | Compd. (A) no. | Chelating agent (B) added | (B)/(A) by mol | Surfactant (C) used | (A)/(B)/(C) by wt. |
|---|---|---|---|---|---|---|
| Invention product | 19 | 7 | EDTA-4Na | 0.33 | — | 80/20/0 |
| | 20 | 7 | EDTA-4Na | 0.30 | POE(10) oleate | 70/15/15 |
| | 21 | 7 | glycine | 12.10 | *POE(10) nonylphenyl ether **POE(20) lauryl ether sulfate sodium | * ** 60/20/(15/5) |
| | 22 | 8 | NTA-3Na | 1.00 | — | 80/20/0 |
| | 23 | 8 | NTA-3Na | 0.57 | POE(8) oleyl ether | 70/10/20 |
| | 24 | 8 | methionine | 2.35 | *POE(8) oleyl ether **sodium dodecylbenzenesulfonate | * ** 60/20/(15/5) |
| | 25 | 9 | ETA-OH | 0.38 | — | 80/20/0 |
| | 26 | 9 | ETA-OH | 0.29 | POE(6) sorbitan monolaurate | 70/15/15 |
| | 27 | 9 | ETA-OH | 0.29 | POE(10) nonylphenyl ether | 70/15/15 |
| | 28 | 10 | methionine | 0.87 | — | 80/20/0 |
| | 29 | 10 | methionine | 0.54 | POE(9) nonylphenyl ether | 70/10/20 |
| | 30 | 10 | ETA-OH | 0.22 | POE(20) sorbitan monooleate | 70/10/20 |
| | 31 | 11 | cysteine | 1.70 | — | 80/20/0 |
| | 32 | 11 | cysteine | 0.88 | POE(6) lauryl ether | 70/10/20 |
| | 33 | 11 | cysteine | 2.13 | *POE(6) lauryl ether **POE(20) lauryl ether sulfate sodium | * ** 60/20/(15/5) |
| | 34 | 12 | malic acid | 0.82 | — | 80/20/0 |
| | 35 | 12 | citric acid | 1.72 | *POE(6) sorbitan monooleate **POE(10) lauryl ether sulfate sodium | * ** 60/12/(2/26) |
| | 36 | 12 | EDTA-4Na | 1.06 | POE(20) sorbitan monooleate | 60/30/10 |
| | 37 | 13 | sodium gluconate | 1.67 | — | 75/25/0 |
| | 38 | 13 | sodium heptonate | 1.33 | POE(15) palm oil fatty acid glyceride | 60/14/26 |
| | 39 | 13 | oxalic acid | 7.41 | — | 75/25/0 |
| | 40 | 13 | EDTA-4Na | 0.88 | POE(15) palm oil fatty acid | 50/10/40 |
| | 41 | 13 | EDTA-4Na | 0.88 | *POE(15) palm oil fatty acid glyceride **POE(10) lauryl ether acetate sodium | * ** 50/10/(10/30) |

TABLE 4-continued

| Formulation no. | Compd. (A) no. | Chelating agent (B) added | (B)/(A) by mol | Surfactant (C) used | (A)/(B)/(C) by wt. |
|---|---|---|---|---|---|
| 42 | 13 | EDTA-4Na | 0.88 | POE(10) lauryl ether acetate sodium | 50/10/40 |
| Comp. product 43 | 6 | — | — | — | 100/0/0 |
| 44 | — | EDTA-4Na | — | — | 0/100/0 |

Chemical formulae of the chelating agents (B) listed in Tables 3, 4-1 and 4-2 are as follows:

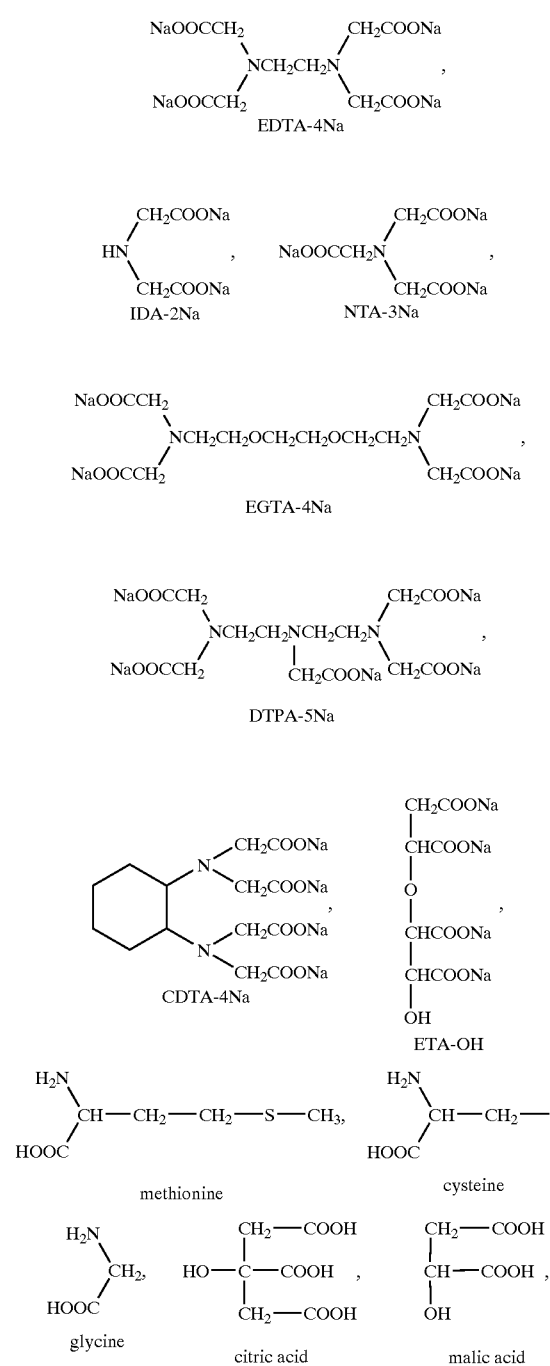

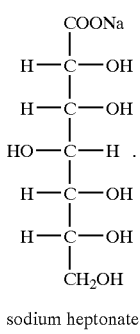

sodium gluconate sodium heptonate

The above-mentioned enhancer compositions listed in Tables 3, 4-1 and 4-2 were each dissolved in deionized water to give a 0.05% by weight [as sum total of compound (A), chelating agent (B) and surfactant (C)] dilution. With the use of the 0.05% by weight dilution thus obtained, commercially available herbicides, i.e., Karmex wettable powder (containing 78.5% by weight of DCMU as the active ingredient), Herbiace liquid formulation (containing 20% by weight of Bialaphos as the active ingredient) and Roundup liquid formulation (containing 41% by weight of isopropylamine salt of Glyphosate as the active ingredient) were each diluted 500-fold. Thus three agricultural chemical compositions were obtained for each enhancer composition for agricultural chemicals.

Fertile soil obtained from a paddy field, gravels (i.e., river sand) and a culture soil available on the market were mixed one another at the weight ratio of 7:2:1. Pots having an inside diameter of 12 cm were filled with the soil thus obtained. In order to conduct a glasshouse-test, the seeds of crabgrass were sowed in the pots and germinated. The pots wherein the growth of the crabglass was abnormal were abandoned to reduce the irregularity among pots. The pots wherein crabgrasses had been grown at a height of about 18 cm were used in the test. Spray gun (mf. by Iwata Tosoki Kogyo K.K., type RG) was used for the application of the agricultural chemical compositions to the crabgrasses. The crabgrasses in the pots were uniformly sprayed with each of the agricultural chemical compositions at a ratio corresponding to 1000 l/ha (liter per hectare) to evaluate the herbicidal efficacy.

On the tenth day after the application, the above-ground part of the fresh plant was weighed and the result was expressed in a herbicidal ratio on the basis of the fresh weight of the above-ground part in the untreated lot (see the following formula).

$$\text{Herbicidal ratio (\%)} = \frac{\begin{pmatrix} \text{above-ground} \\ \text{fresh weight} \\ \text{(g) of an} \\ \text{untreated lot} \end{pmatrix} - \begin{pmatrix} \text{above-ground} \\ \text{fresh weight} \\ \text{(g) of a} \\ \text{test lot} \end{pmatrix}}{\text{above-ground fresh weight}} \times 100$$
$$\text{(g) of an untreated lot}$$

Tables 5, 6-1 and 6-2 show the herbicidal ratios of the agricultural chemical compositions.

TABLE 5

|  |  | Herbicidal ratio (%) | | |
| --- | --- | --- | --- | --- |
|  | Formulation no. | Karmex wettable powder | Herbiace liquid formulation | Roundup liquid formulation |
| Invention product | 1 | 72.1 | 81.4 | 85.3 |
|  | 2 | 75.6 | 82.5 | 89.4 |
|  | 3 | 75.6 | 80.3 | 88.4 |
|  | 4 | 80.1 | 83.9 | 86.5 |
|  | 5 | 83.3 | 85.8 | 90.2 |
|  | 6 | 82.4 | 89.1 | 86.3 |
|  | 7 | 73.1 | 87.2 | 82.4 |
|  | 8 | 77.5 | 85.6 | 85.6 |
|  | 9 | 72.5 | 88.9 | 83.4 |
|  | 10 | 78.5 | 85.8 | 81.5 |
|  | 11 | 75.4 | 87.2 | 84.2 |
|  | 12 | 78.5 | 85.8 | 85.5 |
|  | 13 | 80.3 | 90.1 | 92.1 |
|  | 14 | 78.5 | 89.8 | 91.5 |
|  | 15 | 79.1 | 88.3 | 93.6 |
|  | 16 | 74.5 | 92.4 | 87.2 |
|  | 17 | 77.8 | 90.5 | 90.3 |
|  | 18 | 79.1 | 91.3 | 89.4 |

TABLE 6

|  |  | Herbicidal ratio (%) | | |
| --- | --- | --- | --- | --- |
|  | Formulation no. | Karmex wettable powder | Herbiace liquid formulation | Roundup liquid formulation |
| Invention product | 19 | 71.5 | 78.5 | 79.6 |
|  | 20 | 73.0 | 76.7 | 80.0 |
|  | 21 | 75.8 | 80.8 | 76.7 |
|  | 22 | 76.9 | 85.3 | 91.0 |
|  | 23 | 78.1 | 82.4 | 87.3 |
|  | 24 | 77.9 | 85.3 | 84.9 |
|  | 25 | 75.4 | 81.5 | 90.3 |
|  | 26 | 79.3 | 83.5 | 93.5 |
|  | 27 | 79.2 | 88.7 | 92.5 |
|  | 28 | 73.8 | 88.8 | 78.9 |
|  | 29 | 77.6 | 87.1 | 83.5 |
|  | 30 | 77.6 | 85.9 | 82.8 |
|  | 31 | 79.8 | 84.2 | 80.5 |
|  | 32 | 80.5 | 88.2 | 82.4 |
|  | 33 | 83.0 | 86.5 | 79.8 |
|  | 34 | 79.6 | 87.5 | 91.4 |
|  | 35 | 76.3 | 86.5 | 90.6 |
|  | 36 | 80.2 | 89.2 | 93.8 |
|  | 37 | 81.2 | 84.6 | 90.6 |
|  | 38 | 75.4 | 83.2 | 93.0 |
|  | 39 | 80.3 | 88.5 | 95.4 |
|  | 40 | 70.8 | 79.6 | 82.4 |
|  | 41 | 78.2 | 84.0 | 90.4 |
|  | 42 | 70.2 | 77.2 | 80.2 |

TABLE 6-continued

|  |  | Herbicidal ratio (%) | | |
| --- | --- | --- | --- | --- |
|  | Formulation no. | Karmex wettable powder | Herbiace liquid formulation | Roundup liquid formulation |
| Comp. product | 43 | 53.2 | 59.4 | 65.8 |
|  | 44 | 39.8 | 51.0 | 54.7 |
| Added none |  | 39.8 | 50.6 | 52.3 |

Example 2

Female imagines of *Tetranychus kanzawai kishida* were planted onto kidney bean leaf disks at a ratio of 30 imagines per lot on three runs and then incubated at 25° C. for 24 hours. Subsequently, the whole leaf disks were dipped in a test solution for 5 seconds. After taking out of the test solution and allowing to stand at 25° C. for 48 hours, the leaf disks were observed and the miticidal ratios thereof were determined on the basis of the result in the untreated lot (refer to the following equation).

$$\text{Miticidal ratio (\%)} = \frac{\begin{pmatrix} \text{the number of} \\ \text{living mites of} \\ \text{an untreated lot} \end{pmatrix} - \begin{pmatrix} \text{the number of} \\ \text{living mites of} \\ \text{a test lot} \end{pmatrix}}{\text{the number of living mites of}} \times 100$$
$$\text{an untreated lot}$$

As miticides, Nissorun V emulsion (containing 55% by weight of active ingredients including 50% by weight of hexythiazox and 5% by weight of DDVP) and Osadan wettable powder 25 (containing 25% by weight of phenbutatin oxide as the active ingredient) were each diluted 3,000-fold with the use of deionized water, and the dilutions thus obtained were used. The same enhancer compositions for agricultural chemicals as those employed in Example 1 were used. The concentration of each enhancer composition for agricultural chemicals [i.e., sum total of compound (A), chelating agent (B) and surfactant (C)] in the dilution was adjusted to 0.05% by weight. Further, the above procedure was repeated without using any enhancer compositions. Tables 7, 8-1 and 8-2 show the results.

TABLE 7

|  |  | Miticidal ratio (%) | |
| --- | --- | --- | --- |
|  | Formulation no. | Nissolan V emulsion | Osadan wettable powder 25 |
| Invention product | 1 | 78.9 | 82.2 |
|  | 2 | 83.3 | 85.6 |
|  | 3 | 82.2 | 85.6 |
|  | 4 | 80.0 | 88.9 |
|  | 5 | 82.2 | 87.8 |
|  | 6 | 80.0 | 85.6 |
|  | 7 | 85.6 | 83.3 |
|  | 8 | 83.3 | 82.2 |
|  | 9 | 87.8 | 84.4 |
|  | 10 | 80.0 | 80.0 |
|  | 11 | 78.9 | 80.0 |
|  | 12 | 80.0 | 78.9 |
|  | 13 | 83.3 | 83.3 |
|  | 14 | 85.6 | 82.2 |
|  | 15 | 84.4 | 83.3 |
|  | 16 | 78.9 | 75.6 |

TABLE 7-continued

| Formulation no. | Miticidal ratio (%) | |
|---|---|---|
| | Nissolan V emulsion | Osadan wettable powder 25 |
| 17 | 78.9 | 78.9 |
| 18 | 77.8 | 75.6 |

TABLE 8

| | Formulation no. | Miticidal ratio (%) | |
|---|---|---|---|
| | | Nissolan V emulsion | Osadan wettable powder 25 |
| Invention product | 19 | 84.4 | 87.8 |
| | 20 | 85.6 | 88.9 |
| | 21 | 84.4 | 88.9 |
| | 22 | 83.3 | 80.0 |
| | 23 | 85.6 | 82.2 |
| | 24 | 82.2 | 85.6 |
| | 25 | 78.9 | 82.2 |
| | 26 | 82.2 | 83.3 |
| | 27 | 80.0 | 80.0 |
| | 28 | 86.7 | 82.2 |
| | 29 | 87.8 | 80.0 |
| | 30 | 83.3 | 83.3 |
| | 31 | 77.8 | 76.7 |
| | 32 | 80.0 | 78.9 |
| | 33 | 80.0 | 78.9 |
| | 34 | 80.0 | 80.0 |
| | 35 | 82.2 | 80.0 |
| | 36 | 86.7 | 83.3 |
| | 37 | 82.2 | 80.0 |
| | 38 | 82.2 | 82.2 |
| | 39 | 87.8 | 86.7 |
| | 40 | 70.6 | 76.2 |
| | 41 | 79.2 | 80.6 |
| | 42 | 72.4 | 72.4 |
| Comp. product | 43 | 55.6 | 60.0 |
| | 44 | 42.2 | 44.4 |
| Added none | | 38.9 | 40.0 |

Example 3

Rice planthopper larvae of the third instar were incubated and used in an efficacy test on insecticides in triplicate runs by the dipping method (each lot having 10 larvae). The insecticidal ratio was determined in the same manner as the one employed for the determination of the miticidal ratio. Commercially available insecticides, i.e., Sumithion emulsion (containing 50% by weight of MEP as the active ingredient) and Malathon emulsion (containing 50% by weight of malathon as the active ingredient) were each diluted 3,000-fold with the use of deionized water, and the dilutions thus obtained were used. As the enhancer compositions for agricultural chemicals, those employed in Example 1 were used in such a manner as to adjust the concentration of each enhancer composition [i.e., sum total of compound (A), chelating agent (B) and surfactant (C)] in the diluted solution to 0.1% by weight. Tables 9, 10-1 and 10-2 show the results.

TABLE 9

| | Formulation no. | Insecticidal ratio (%) | |
|---|---|---|---|
| | | Sumithion emulsion | Malathon emulsion |
| Invention product | 1 | 76.7 | 83.3 |
| | 2 | 80.0 | 86.7 |
| | 3 | 76.7 | 83.3 |
| | 4 | 80.0 | 86.7 |
| | 5 | 83.3 | 86.7 |
| | 6 | 83.3 | 90.0 |
| | 7 | 80.0 | 83.3 |
| | 8 | 80.0 | 83.3 |
| | 9 | 80.0 | 86.7 |
| | 10 | 76.7 | 86.7 |
| | 11 | 83.3 | 83.3 |
| | 12 | 83.3 | 86.7 |
| | 13 | 80.0 | 80.0 |
| | 14 | 80.0 | 83.3 |
| | 15 | 83.3 | 83.3 |
| | 16 | 76.7 | 83.3 |
| | 17 | 76.7 | 80.0 |
| | 18 | 73.3 | 90.0 |

TABLE 10

| | Formulation no. | Insecticidal ratio (%) | |
|---|---|---|---|
| | | Sumithion emulsion | Malathon emulsion |
| Invention product | 19 | 86.7 | 86.7 |
| | 20 | 90.0 | 90.0 |
| | 21 | 90.0 | 90.0 |
| | 22 | 80.0 | 90.0 |
| | 23 | 76.7 | 86.7 |
| | 24 | 83.3 | 86.7 |
| | 25 | 90.0 | 86.7 |
| | 26 | 83.3 | 90.0 |
| | 27 | 83.3 | 90.0 |
| | 28 | 76.7 | 83.3 |
| | 29 | 80.0 | 83.3 |
| | 30 | 83.3 | 83.3 |
| | 31 | 83.3 | 80.0 |
| | 32 | 80.0 | 83.3 |
| | 33 | 83.3 | 80.0 |
| | 34 | 76.7 | 76.7 |
| | 35 | 80.0 | 76.7 |
| | 36 | 83.3 | 80.0 |
| | 37 | 80.0 | 83.3 |
| | 38 | 83.3 | 83.3 |
| | 39 | 90.0 | 86.7 |
| | 40 | 72.0 | 75.2 |
| | 41 | 79.6 | 80.0 |
| | 42 | 73.2 | 73.5 |
| Comp. product | 43 | 56.7 | 63.3 |
| | 44 | 46.7 | 50.0 |
| Added none | | 40.0 | 43.3 |

Example 4

Conidia of *Sphaerotheca fuliginea* acquiring the resistance against fungicides were inoculated into young cucumber seedlings at the trifoliate stage at a ratio of $10^8$ per pot, which were then allowed to stand at 25° C. under a relative humidity of 90% for 2 days in the dark.

Then, a marketed fungicide, i.e., Bayleton wettable powder 5 (containing 5% by weight of triadimefon as the active ingredient) was diluted 3,000-fold with the 2,500-fold dilution (diluent: deionized water) of each of the enhancer compositions employed in Example 1. The dilution thus obtained was applied onto the seedlings at a ratio of 5 ml per pot. After allowing the pots to stand at 25° C. under a relative humidity of 85%, lesions were counted and the preventive value was calculated in accordance with the following equation. Tables 11,-12-1 and 12-2 show the results.

$$\text{Preventive value} = \left[1 - \frac{\text{no. of lesions of a test lot}}{\text{no. of lesions of an untreated lot}}\right] \times 100$$

TABLE 11

|  | Formulation no. | Preventive value Bayleton wettable powder 5 |
|---|---|---|
| Invention product | 1 | 89.5 |
|  | 2 | 92.2 |
|  | 3 | 93.3 |
|  | 4 | 92.1 |
|  | 5 | 95.2 |
|  | 6 | 94.8 |
|  | 7 | 85.8 |
|  | 8 | 90.4 |
|  | 9 | 93.5 |
|  | 10 | 94.0 |
|  | 11 | 93.0 |
|  | 12 | 95.4 |
|  | 13 | 85.3 |
|  | 14 | 88.9 |
|  | 15 | 85.3 |
|  | 16 | 90.5 |
|  | 17 | 92.4 |
|  | 18 | 93.8 |

TABLE 12

|  | Formulation no. | Preventive value Bayleton wettable powder 5 |
|---|---|---|
| Invention product | 19 | 95.2 |
|  | 20 | 100.0 |
|  | 21 | 100.0 |
|  | 22 | 91.4 |
|  | 23 | 87.3 |
|  | 24 | 89.4 |
|  | 25 | 91.8 |
|  | 26 | 95.4 |
|  | 27 | 100.0 |
|  | 28 | 88.2 |
|  | 29 | 93.5 |
|  | 30 | 95.1 |
|  | 31 | 90.3 |
|  | 32 | 95.4 |
|  | 33 | 100.0 |
|  | 34 | 92.6 |
|  | 35 | 95.4 |
|  | 36 | 100.0 |
|  | 37 | 82.5 |
|  | 38 | 83.2 |
|  | 39 | 90.6 |
|  | 40 | 80.5 |
|  | 41 | 85.6 |
|  | 42 | 78.2 |
| Comp. product | 43 | 69.8 |
|  | 44 | 57.6 |
| Added none |  | 54.7 |

The above Examples 1 to 4 show tests whereby the efficacies of the enhancer compositions for agricultural chemicals of the present invention were compared with those of common cationic surfactants employed as enhancers for agricultural chemicals or chelating agents.

As Tables 5 to 12-2 clearly show, since the chelating agent further enhanced the effect of at least one nitrogen-containing compound selected from the group consisting of a tertiary amine, a tertiary amine salt and a quaternary ammonium salt in enhancing the efficacy of the agricultural chemicals in the enhancer compositions for agricultural chemicals of the present invention, the enhancer compositions for agricultural chemicals of the present invention exhibited remarkable effects of enhancing the efficacy of the agricultural chemicals.

When a chelating agent was used alone, the efficacy of an agricultural chemical could be somewhat enhanced thereby but the effect could not attain any practically usable level.

Accordingly, it has been found that in the enhancer compositions for agricultural chemicals of the present invention, the chelating agent specifically enhances the effect of at least one nitrogen-containing compound selected from the group consisting of a tertiary amine, a tertiary amine salt and a quaternary ammonium salt of enhancing the efficacy of the agricultural chemicals.

Example 5

The same test as the one effected in Example 1 was carried out by using Roundup liquid formulation (containing 41% by weight of active ingredient) as a herbicide, and the formulation Nos. 13, 27 and 32 of Example 1 as enhancer compositions each in the amount as specified in Table 13. Table 13 shows the results. In Table 13, the term "herbicide concn." means the concentration of the marketed herbicide formulation in a dilution to be applied, the term "enhancer compn. concn." means the concentration of the enhancer composition [i.e. sum total of compound (A), chelating agent (B) and surfactant (C)] in a dilution to be applied, and the term, "agricultural chemical" means the active ingredient(s) of the marketed herbicide formulation.

TABLE 13

| Test no. | Formulation no. | Herbicide concn. (ppm) | Enhancer compn. concn. (ppm) | Agricultural chemical/ enhancer compn. (by wt.) | Herbicidal ratio (%) |
|---|---|---|---|---|---|
| 1 | Formulation no. 13 | 1000 | 50 | 1/0.12 | 80.5 |
| 2 |  | 1000 | 100 | 1/0.24 | 87.4 |
| 3 |  | 1000 | 500 | 1/1.2 | 94.0 |
| 4 |  | 1000 | 1000 | 1/2.4 | 95.8 |
| 5 |  | 1000 | 5000 | 1/12 | 94.2 |
| 6 |  | 1000 | 10000 | 1/24 | 89.2 |
| 7 | Formulation no. 27 | 1000 | 50 | 1/0.12 | 82.3 |
| 8 |  | 1000 | 100 | 1/0.24 | 90.4 |
| 9 |  | 1000 | 500 | 1/1.2 | 93.5 |
| 10 |  | 1000 | 1000 | 1/2.4 | 96.2 |
| 11 |  | 1000 | 5000 | 1/12 | 96.0 |
| 12 |  | 1000 | 10000 | 1/24 | 90.5 |
| 13 | Formulation no. 32 | 1000 | 50 | 1/0.12 | 78.4 |
| 14 |  | 1000 | 100 | 1/0.24 | 80.8 |
| 15 |  | 1000 | 500 | 1/1.2 | 84.5 |
| 16 |  | 1000 | 1000 | 1/2.4 | 88.9 |
| 17 |  | 1000 | 5000 | 1/12 | 87.8 |
| 18 |  | 1000 | 10000 | 1/24 | 88.0 |
| 19 | — | 1000 | 0 | — | 55.2 |

Example 6

The enhancer compositions for agricultural chemicals listed in Table 14 were prepared by adding an adjuvant for penetration to each of the enhancer compositions listed in Tables 4-1 and 4-2.

The above-mentioned enhancer compositions for agricultural chemicals listed in Table 14 were each dissolved in deionized water to give a 0.05% by weight [as sum total of compound (A), chelating agent (B) and surfactant (C)] dilution. With the use of the 0.05% by weight dilution thus obtained, commercially available herbicides, i.e., Karmex wettable powder (containing 78.5% by weight of DCMU as the active ingredient), Herbiace liquid formulation (containing 20% by weight of Bialaphos as the active ingredient) and Roundup liquid formulation (containing 41% by weight of isopropylamine salt of Glyphosate as the active ingredient) were each diluted 700-fold. Thus three agricultural chemical compositions were obtained for each enhancer composition for agricultural chemicals.

The same test as the one effected in Example 1 was carried out by using the agricultural chemical compositions thus obtained, and their herbicidal ratios were determined. Table 15 show the results.

TABLE 14

| | Formulation no. | Base formulation no. | Adjuvant for penetration (D) added | (A + B + C)/(D) by wt. | (A)/(B) by wt. |
|---|---|---|---|---|---|
| Invention product | 45 | 22 | diethylene glycol monobutyl ether | 1/0.5 | 1/0.63 |
| | 46 | 34 | POE(3) phenol | 1/0.8 | 1/1 |
| | 47 | 37 | 2-ethylhexyl oleate | 1/0.7 | 1/0.93 |
| | 48 | 41 | diethylene glycol monobutyl ether | 1/1 | 1/2 |
| Comp. product | 49 | 43 | polyethylene glycol (degree of polymerization: 400) | 1/1 | 1/1 |
| | 50 | 44 | diethylene glycol monobutyl ether | 1/1 | 0 |

TABLE 15

| | Formulation no. | Herbicidal ratio (%) | | |
|---|---|---|---|---|
| | | Karmex wettable powder | Herbiace liquid formulation | Roundup liquid formulation |
| Invention product | 45 | 69.4 | 74.2 | 80.4 |
| | 46 | 68.8 | 74.0 | 78.6 |
| | 47 | 70.6 | 76.5 | 82.1 |
| | 48 | 73.2 | 82.1 | 86.3 |
| Comp. product | 49 | 45.3 | 49.8 | 56.2 |
| | 50 | 32.4 | 40.2 | 43.6 |
| Added none | | 31.6 | 38.4 | 40.6 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:
1. An agricultural chemical composition, comprising:
(a) an agricultural chemical;
(b) a nitrogen-containing compound of the formula:

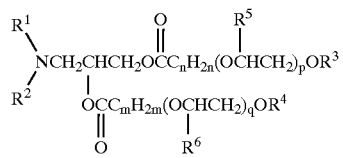

wherein $R^1$ and $R^2$ are the same or different from each other and each represents an alkyl group having 1 to 4 carbon atoms which may be substituted by a hydroxyl group; $R^3$ and $R^4$ are the same or different from each other and each represents a linear or branched alkyl or alkenyl group having 4 to 36 carbon atoms which may be substituted by a hydroxyl group; each $R^5$ represents a hydrogen atom or a methyl group; each $R^6$ represents a hydrogen atom or a methyl group; m and n are the same or different from each other and each represents a positive number of 1 to 5; and p and q, which each represents an average value, are either the same or different from each other and each represents a number of 0 to 30, or an inorganic organic salt thereof; and
c) a chelating agent selected from the group consisting of amino polycarboxylic acid chelating agents or salt thereof, aromatic carboxylic acid chelating agents or salt thereof, a salt of aliphatic carboxylic acid chelating agents, amino acid chelating agents or salt thereof, ether polycarboxylic acid chelating agents or salt thereof, phosphonic acid chelating agents or salt thereof, a salt of hydroxy carboxylic acid chelating agents, polymer or oligomer electrolyte chelating agents, dimethylglyoxime (DG), ascorbic acid or a salt thereof, and thioglycollic acid or a salt thereof;
wherein the content of the chelating agent ranges from 0.01 to 30 mol per mol of the nitrogen-containing compound and the weight ratio of the total of the nitrogen-containing compound and the chelating agent to the agricultural chemical ranges from 0.05 to 50.

2. An agricultural chemical composition, comprising:
(a) an agricultural chemical;
(b) a nitrogen-containing compound of the formula:

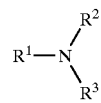

wherein $R^1$ represents an alkyl group having 1 to 4 carbon atoms which may be substituted by a hydroxyl group;
$R^2$ represents a linear or branched alkyl group having 1 to 36 carbon atoms which may be substituted by a hydroxyl group or a linear or branched alkenyl group having 2 to 36 carbon atoms which may be substituted by a hydroxyl group, a group represented by the formula: —$CH_nH_{2n}$—OCO—$R^4$ or —$C_nH_{2n}$—NHCO—$R^4$ (wherein $R^4$ represents a linear or branched alkyl or alkenyl group having 5 to 36 carbon atoms which may be substituted by a hydroxyl group; and n represents a positive number of 2 to 6), a group represented by the formula:

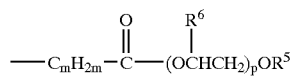

(wherein $R^5$ represents a linear or branched alkyl or alkenyl group having 6 to 36 carbon atoms which may be substituted by a hydroxyl group; each $R^6$ represents a hydrogen atom or a methyl group; m is a positive number of 1 to 5; and p is a number of 0 to 30) or a group represented by the formula:

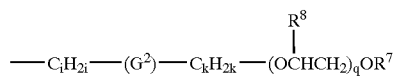

(wherein $R^7$ represents a linear or branched alkyl or alkenyl group having 4 to 36 carbon atoms which may be substituted by a hydroxyl group; each $R^8$ represents a hydrogen atom or a methyl group; $G^2$ represents a group represented by the formula: —OCO— or a group represented by the formula: —NHCO—; i represents a positive number of 2 to 6; k represents a positive number of 1 to 5; and q represents a number of 0 to 30); and $R^3$ represents a group represented by the formula:

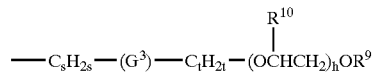

(wherein $R^9$ represents a linear or branched alkyl or alkenyl group having 4 to 36 carbon atoms which may be substituted by a hydroxyl group; each $R^{10}$ represents a hydrogen atom or a methyl group; $G^3$ represents a group represented by the formula: —OCO— or a group represented by the formula: —NHCO—; s represents a positive number of 2 to 6; t represents a positive number of 1 to 5; and h represents a positive number of 0 to 30) or a group represented by the formula:

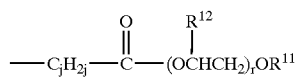

(wherein $R^{11}$ represents a linear or branched alkyl or alkenyl group having 6 to 36 carbon atoms which may be substituted by a hydroxyl group; each $R^{12}$ represents a hydrogen atom or a methyl group; j represents a positive number of 1 to 5; and r represents a positive number of 0 to 30) or an inorganic or organic salt thereof; and (c) a chelating agent selected from the group consisting of amino polycarboxylic acid chelating agents or salt thereof, aromatic carboxylic acid chelating agents or salt thereof, a salt of aliphatic carboxylic acid chelating agents, amino acid chelating agents or salt thereof, ether polycarboxylic acid chelating agents or salt thereof, phosphonic acid chelating agents or salt thereof, a salt of hydroxy carboxylic acid chelating agents, polymer or oligomer electrolyte chelating agents, dimethylglyoxime (DG), ascorbic acid or a salt thereof, and thioglycollic acid or a salt thereof;

wherein the content of the chelating agent ranges from 0.01 to 30 mol per mol of the nitrogen-containing compound and the weight ratio of the total of the nitrogen-containing compound and the chelating agent to the agricultural chemical ranges from 0.05 to 50.

3. An agricultural chemical composition, comprising:

(a) an agricultural chemical;

(b) a nitrogen-containing compound of the formula:

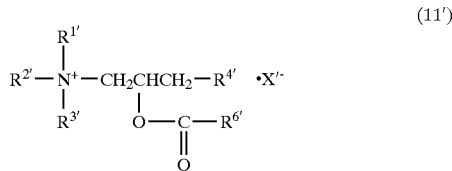

(11')

wherein $R^{1'}$ to $R^{3'}$ are either the same or different from each another and each represents an alkyl or hydroxyalkyl group having 1 to 4 carbon atoms, $R^{4'}$ represents a group represented by the formula: —OCOR, wherein R represents an alkyl or alkenyl group having 14 to 22 carbon atoms, $R^{6'}$ represents an alkyl or alkenyl group having 14 to 22 carbon atoms, and $X^-$ is a counter ion derived from a strong acid; and (c) a chelating agent selected from the group consisting of amino polycarboxylic acid chelating agents or salt thereof, aromatic carboxylic acid chelating agents or salt thereof, a salt of aliphatic carboxylic acid chelating agents, amino acid chelating agents or salt thereof, ether polycarboxylic acid chelating agents or salt thereof, phosphonic acid chelating agents or salt thereof, a salt of hydroxy carboxylic acid chelating agents, polymer or oligomer electrolyte chelating agents, dimethylglyoxime (DG), ascorbic acid or a salt thereof, and thioglycollic acid or a salt thereof;

wherein the content of the chelating agent ranges from 0.01 to 30 mol per mol of the nitrogen-containing compound and the weight ratio of the total of the nitrogen-containing compound and the chelating agent to the agricultural chemical ranges from 0.05 to 50.

4. The agricultural chemical composition according to claim 1, 2 or 3, wherein said agricultural chemical composition further comprises a surfactant other than said nitrogen-containing compound.

5. The agricultural chemical composition of claim 4, wherein the weight ratio of the nitrogen-containing compound to the surfactant other than the nitrogen-containing compound ranges from 1/10 to 50/1.

6. The agricultural chemical composition of claim 1, 2 or 3, wherein said agricultural chemical composition further comprises an adjuvant for penetration of agricultural chemicals.

7. The agricultural chemical composition of claim 6, wherein the weight ratio of the nitrogen-containing compound to the adjuvant ranges from 1/5 to 5/1.

8. The composition according to claim 3, wherein the counter ion $X^-$ is a halide, acetate, methyl sulfate, ethylsulfate, a phosphate group, a phosphonate group, a sulfonate group having a hydrocarbon moiety with at least 7 carbon atoms, a sulfate group having a hydrocarbon moiety with at least 7 carbon atoms, or an anionic oligomer or copolymer having a degree of polymerization of at least 3 and having an anionic residue, an anionic oligomer or polymer having an average molecular weight of 300 to 20,000 and having an acidic anionic residue.

9. The composition according to claim 1, 2 or 3, wherein said agricultural chemical composition further comprises an ingredient selected from the group consisting of a pH regulator, an inorganic salt, a thickener, a plant growth regulator, fertilizer and a preservative.

* * * * *

UNITED STATES PATENT AND TRADEMARK OFFICE
CERTIFICATE OF CORRECTION

PATENT NO. : 6,706,666 B2
DATED : March 16, 2004
INVENTOR(S) : Hasebe et al.

It is certified that error appears in the above-identified patent and that said Letters Patent is hereby corrected as shown below:

Title page,
Item [63], Related U.S. Application Data, change "(63) Continuation of application No. 08/507,483, filed as application No. PCT/JP94/02263 on Dec. 27, 1974, now abandoned." to -- (63) Continuation of application No. 08/507,483, filed as application No. PCT/JP94/02263 on Dec. 27, 1994, now abandoned. --

Signed and Sealed this

Twelfth Day of October, 2004

JON W. DUDAS
*Director of the United States Patent and Trademark Office*